(12) United States Patent
Costantino et al.

(10) Patent No.: US 11,056,245 B2
(45) Date of Patent: Jul. 6, 2021

(54) SYSTEMS AND METHODS FOR TRANSITIONS OF CARE

(71) Applicants: Peter Costantino, Westport, CT (US); Michael Gilvary, New York, NY (US)

(72) Inventors: Peter Costantino, Westport, CT (US); Michael Gilvary, New York, NY (US)

(73) Assignee: IDION LLC, New York, NY (US)

( * ) Notice: Subject to any disclaimer, the term of this patent is extended or adjusted under 35 U.S.C. 154(b) by 27 days.

(21) Appl. No.: 16/721,389

(22) Filed: Dec. 19, 2019

(65) Prior Publication Data

US 2020/0126660 A1 Apr. 23, 2020

Related U.S. Application Data

(63) Continuation-in-part of application No. 16/140,080, filed on Sep. 24, 2018, now Pat. No. 10,810,479, (Continued)

(51) Int. Cl.
*G16H 80/00* (2018.01)
*G16H 10/60* (2018.01)
(Continued)

(52) U.S. Cl.
CPC ........... *G16H 80/00* (2018.01); *G06K 7/1417* (2013.01); *G06K 19/02* (2013.01);
(Continued)

(58) Field of Classification Search
CPC ........ G16H 80/00; G16H 10/65; G16H 10/60; G09F 3/0292; G06K 19/077; G06K 19/02; G06K 19/06046; G06K 7/1417
See application file for complete search history.

(56) References Cited

U.S. PATENT DOCUMENTS 6,635,326 B2 * 10/2003 Ueki ...................... B42D 15/00
40/324
2003/0176785 A1 * 9/2003 Buckman .............. A61B 5/1112
600/431

(Continued)

*Primary Examiner* — Christle I Marshall
(74) *Attorney, Agent, or Firm* — Anthony H. Handal; Mona Roy; Handal & Morofsky

(57) ABSTRACT

A system and method to manage the transitioning the care of an individual in a healthcare setting from one point of care with a particular set of characteristics to another physical location with a different set of characteristics by providing for the retrieval of information relating to an individual by a plurality of authorized users and devices at multiple facilities. The system includes a skin wearable, waterproof, non-transferable frangible individual identification device comprising an adhesive and an ink arranged to provide a physiologically and optically perceptible, humanly understandable, and machine readable information relating to said individual wherein once applied to skin said identification device is not removable in one piece without rendering the device inoperable; a plurality of reader devices; a computer interface device receiving information from said individual identification device and from said reader devices respecting the individual identified by said individual identification device; a computer system coupled to said computer interface device, said computer system including a memory with an algorithm for processing information collected by said computer system; and a separate set of reader devices and a separate service rendering system, each output information from their respective reader devices to a common database, the contents of said common database being coupled to a computing device which communicates information to said plurality of facilities.

29 Claims, 11 Drawing Sheets

Related U.S. Application Data which is a continuation-in-part of application No. 15/699,427, filed on Sep. 8, 2017, now Pat. No. 10,083,391, which is a continuation-in-part of application No. 15/295,144, filed on Oct. 17, 2016, now Pat. No. 9,996,789, which is a continuation-in-part of application No. 14/862,033, filed on Sep. 22, 2015, now Pat. No. 9,519,724, and a continuation-in-part of application No. 14/862,081, filed on Sep. 22, 2015, now abandoned, and a continuation-in-part of application No. 14/860,646, filed on Sep. 21, 2015, now Pat. No. 9,489,466.

(60) Provisional application No. 62/882,094, filed on Aug. 2, 2019, provisional application No. 62/880,262, filed on Jul. 30, 2019, provisional application No. 62/875,684, filed on Jul. 18, 2019, provisional application No. 62/825,514, filed on Mar. 28, 2019, provisional application No. 62/793,293, filed on Jan. 16, 2019, provisional application No. 62/690,413, filed on Jun. 27, 2018, provisional application No. 62/690,341, filed on Jun. 26, 2018, provisional application No. 62/618,782, filed on Jan. 18, 2018, provisional application No. 62/580,952, filed on Nov. 2, 2017, provisional application No. 62/531,863, filed on Jul. 12, 2017, provisional application No. 62/500,419, filed on May 2, 2017, provisional application No. 62/426,765, filed on Nov. 28, 2016, provisional application No. 62/377,786, filed on Aug. 22, 2016, provisional application No. 62/375,892, filed on Aug. 16, 2016, provisional application No. 62/365,988, filed on Jul. 23, 2016, provisional application No. 62/359,104, filed on Jul. 6, 2016, provisional application No. 62/357,240, filed on Jun. 30, 2016, provisional application No. 62/242,973, filed on Oct. 16, 2015, provisional application No. 62/053,725, filed on Sep. 22, 2014.

(51) Int. Cl.

| | | |
|---|---|---|
| *G06K 19/02* | (2006.01) | |
| *G09F 3/00* | (2006.01) | |
| *G06K 7/14* | (2006.01) | |
| *G16H 10/65* | (2018.01) | |
| *G06K 19/077* | (2006.01) | |
| *G06K 19/06* | (2006.01) | |
| *G16H 40/20* | (2018.01) | |
| *G16H 70/20* | (2018.01) | |
| *G16H 70/40* | (2018.01) | |
| *G16H 20/10* | (2018.01) | |
| *G16H 40/67* | (2018.01) | |

(52) U.S. Cl.
CPC ..... *G06K 19/06046* (2013.01); *G06K 19/077* (2013.01); *G09F 3/0292* (2013.01); *G16H 10/60* (2018.01); *G16H 10/65* (2018.01); *G16H 20/10* (2018.01); *G16H 40/20* (2018.01); *G16H 40/67* (2018.01); *G16H 70/20* (2018.01); *G16H 70/40* (2018.01)

(56) References Cited

U.S. PATENT DOCUMENTS

| | | | | |
|---|---|---|---|---|
| 2005/0196573 | A1* | 9/2005 | Myers | G09F 3/0292 428/40.1 |
| 2007/0029377 | A1* | 2/2007 | Hinckley | G06K 19/041 235/380 |
| 2012/0107543 | A1* | 5/2012 | Pickett | B44C 1/105 428/41.8 |
| 2013/0290013 | A1* | 10/2013 | Forrester | G16H 10/65 705/2 |
| 2014/0207686 | A1* | 7/2014 | Experton | G16H 40/20 705/51 |
| 2015/0053759 | A1* | 2/2015 | Cahill, Jr. | G06F 16/24 235/380 |

* cited by examiner

SYSTEMS AND METHODS FOR TRANSITIONS OF CARE

CROSS REFERENCE TO RELATED APPLICATIONS

This application is a continuation of U.S. patent application Ser. No. 15/699,427 Visually, Optically and electronically Readable Frangible Device for Affixation to the Skin filed Sep. 8, 2017 and continuation-in-part of International Application No. PCT/US2015/051289, entitled, Security and Accounting Infrastructure, and Associated Cutaneous Information Device and Method, filed on Sep. 22, 2015, which claims priority to U.S. Provisional Application No. 62/053,725, entitled, Temporary Cutaneous Information Device and Associated Method and Multi-Patient Treatment Infrastructure, filed on Sep. 22, 2014. This application also claims priority of International Application PCT/US2017/048085, entitled, Improved Visually, Optically and Electronically Readable Frangible Device for Affixation to the Skin, filed on Aug. 22, 2017, as well as applications International Application PCT/US2017/040053 System and Method for Transitions of Care, filed Jun. 29, 2017, U.S. patent application Ser. No. 14/860,646, Transportation and Resort Infrastructure, and Associated Cutaneous Information Device and Method, filed Sep. 21, 2015, U.S. patent application Ser. No. 14/862,033, Temporary Cutaneous Information Device and Associated Method and Multi-Patient Treatment Infrastructure and U.S. patent application Ser. No. 14/862,081 Temporary Cutaneous Information Device, Associated Method and Resort Infrastructure both filed on Sep. 22, 2015, U.S. Provisional Patent Application No. 62/242,973 Method and Apparatus for Manufacturing Cutaneous Information Devices, filed Oct. 16, 2015, U.S. Provisional Application No. 62/357,240 Transitions of Care Information Device, filed on Jun. 30, 2016, U.S. Provisional Application No. 62/359,104 Skin Applied Point of Service Preparation Device Process and Design Technical Field, filed on Jul. 6, 2016, U.S. Provisional Application No. 62/365,988 Method for the Biocompatible Skin Safe Application of Multiple Color Images to the Skin filed Jul. 23, 2016, U.S. Provisional Application No. 62/375,892 Method For Biocompatible Skin Safe Application of One or More Color Images To the Skin Using Sublimation Printing, filed Aug. 16, 2016, U.S. Provisional Patent Application No. 62/377,786 entitled Improved Visually, Optically and Electronically Readable Device for Durable Affixation to the Skin filed on Aug. 22, 2016, U.S. patent application Ser. No. 15/295,144 Method and Apparatus for Manufacturing Cutaneous Information Devices, filed Oct. 17, 2016, U.S. Provisional Patent Application No. 62/426,765 Method For Biocompatible Skin Safe Application of One or More Color Images To The Skin Using Thermal Printing, filed on Nov. 28, 2016, U.S. Provisional Patent Application No. 62/500,419 Construct Design and Application of Cutaneous Information Device for Enhanced Physical Authentication Including a Streamlined Digital Authentication Process, filed May 2, 2017, U.S. Provisional Patent Application No. 62/531,863 Nontransferable Identification Device, filed Jul. 12, 2017. additionally, priority is claimed to U.S. Provisional Patent Application No. 62/580,952 Customizable Cutaneous Information Devices and Manufacturing Methods for the Same filed Nov. 2, 2017, and U. S. Provisional Patent Application No. 62/618,782 Cost Effective Cutaneous Information Devices With Enhanced Frangibility filed Jan. 18, 2018, U. S. Provisional Patent Application No. 62/690,341, Enhanced Cutaneous Information Device With Proximity Detection filed Jun. 26, 2018, U. S. Provisional Patent Application No. 62/690,413 Cutaneous Information Device System with Wireless Detection of Patron Location filed on Jun. 27, 2018, U. S. Provisional Patent Application No. 62/793,293 Improvements To Cutaneous Information Device Structure filed on Jan. 16, 2019, U.S. Provisional Patent Application No. 62/825,514 Cutaneous Smart Tag With Redundant Electronic/Visual Security Mechanism filed on Mar. 28, 2019, U.S. Provisional Patent Application No. 62/875,684 entitled Systems For Point of Service Customization and Printing of Non Transferable Cutaneous Identification Devices Using Thermal Transfer Printing filed on Jul. 18, 2019, U.S. Provisional Patent Application No. 62/880,262 entitled Systems for Secure Identification Using Cutaneous Smart Tags with Redundant Electronic/Visual Security Mechanisms filed on Jul. 30, 2019, the disclosures of all of the above are incorporated herein by reference.

TECHNICAL FIELD

This invention relates to the apparatus and methods for transitioning the care of an individual in a healthcare setting from one point of care with a particular set of characteristics to the another physical location, internal or external with a different set of characteristics while maintaining safety and quality of care using a frangible, non transferable cutaneous skin bonded identification device as the nexus point for patient identification, interaction, information exchange, and administration allowing the connection of disparate systems and facilitating a safe and reliable transition system.

BACKGROUND OF THE INVENTION

Currently healthcare facilities, including but not limited to hospitals, emergency rooms, rehabilitation and surgery centers, focus on offering the highest level of care during a patient visit. However, at discharge, patients typically are given a verbal instruction regarding post discharge treatment, medication and self-care, a stack of medical papers and a website which serves as a depository for medical files and data, however does little to manage the patients care. The patient is discharged from the hospital into an uncontrolled environment ill-equipped for the challenges ahead. Often, patients retain very little verbal instruction from the healthcare staff and the volume of documentation can be generic and overwhelming making it difficult for a patient to ascertain which information is most relevant to said individual during a dynamic period of changing parameters and circumstances. This failed exercise results in confusion at home or alternate facility, stress, mismanaged self-care and avoidable costly mistakes and even readmissions to the healthcare facility.

In many cases, these individuals are transferred to another facility for example, emergency room, specialist, inpatient care center, outpatient care center to any other facility to receive a particular type of care that is not expertise of the current location or the services needed are not readily as available. In this type of situation, the patient is expected to physically move locations often tasked with being the courier of their own health information as they transfer to the other facility. Even when transferred within the same healthcare system these transitions can be cumbersome and inefficient since the patient, often in a compromised state, is heavily relied upon remember detailed instruction, scheduling and location information while keeping track of documentation supplied throughout the treatment process.

Prior art systems have several deficiencies. For example, the process currently relies heavily on the patient being treated to relay information either physically by carrying paperwork or verbally by sharing information with the facility when they arrive. Furthermore, the communication between facilities can be disjointed making it even more difficult for the facility to swiftly and correctly transition the care of an individual from one facility to another.

The process as it stands now is quite inefficient where higher wage resources such as care providers (i.e. physicians, physicians assistants and nurses), radiology technicians and other skilled employees are tasked or pulled from core functions to execute clerical tasks, paperwork and other organizational tasks as a result of mismanagement and attempt to assist the patients. These inefficiencies result in unnecessarily increased costs, as simple tasks such as identification and patient transfer require the assistance of specialty higher wage employees. This puts a strain on the system by pulling valuable resources from the primary task to compensate for the challenges associated with the transition of care. Thus, healthcare facilities are forced to hire extra staff, to compensate for the additional workload or deliver a lower level of care in order to manage this process. This takes time and money away from the primary function of a healthcare facility and its staff. Furthermore, the discharge dates and times are often unpredictable due to a myriad of factors and thus making it impossible for a medical facility to predict when extra staffing will be needed to care for patients in one of the most critical, mismanaged and overlooked parts of the healthcare process, the transition of care.

This can also create frustration among the providers and staff while trying to manage their duties and dealing with a confused patient trying to sift through a stack of medical documentation to answer a question. Meanwhile the patient or their caregiver tries to absorb as much information as possible to execute the home care plan for example, sometimes without being given the proper tools to complete the task efficiently and correctly. This confusion has a direct impact on the patient's ability to absorb information during a transition related to his or her own care and self-management of health. The result is re-admission and low patient satisfaction both of which puts significant financial strain on a healthcare facility.

When a patient is discharged and sent home the same issues occur but with the further burden of previously available hospital supports. The under supported transfer from hospital to home results in expensive and time-consuming readmissions. These events are often preventable and are the result of miscommunications hospital to home.

As a result of the delays, inefficient use of resources and the haphazard approach to medical management staff and patients are put under a significant amount of stress and ultimately all of these risk factors combined can result in medical error. It is reasonable to assume in this type of environment that information can be misunderstood, misinterpreted and transferred incorrectly putting the patient at risk. This hit or miss system is a result of healthcare management by department. Healthcare departments often run in silos, radiology is a completely different department than surgery with its own goals and expectations. Even facilities across a health system vary in substantial ways based on location, patient demographics leadership etc. Each part of the hospital and each department and each facility essentially act independently. In this confusion, the patient suffers and avoidable mistakes are made. A system is needed which shifts the focus of the care from the various facilities and its operations to the patient.

Companies have worked to provide tablets and other smart devices to help manage patient care at home or across different facilities and help the staff care for the patient outside of the primary healthcare facility. These systems, such as home care monitoring, can be helpful; however, they are working under the assumption the correct patient is using the correct device at the right time. This is very difficult to assume since in a home care setting or an alternative care location, for example, the patient is in an uncontrolled environment and secure identification is nearly impossible without the use of biometrics or cumbersome log in procedures which is a difficult process. There is no way to securely identify the patient outside of the healthcare facility as a way to manage the patient process care as the patient transitions from one location to another regardless of what those locations are. Incumbent systems do not consider the transition of care, meaning where the patient is cared for in one location for a period of time then as the patient leaves one facility which has a certain and specific set of characteristics, personnel, technology, and/or policies to another facility with a unique and often times vastly different set of characteristics. Current systems and solutions look at each individual location and attempt to solve these challenges. Poor transitional care management (sometimes compromised care in transition facilities) often results in re-admission or self-induced medical error. Current systems do not consider the entire care process regardless of the location by making the patient the nexus point in their care not the location where they happen to be, temporarily or long term. There is a need for a system that reliably identifies the patient in any location and allows the secure transfer critical information in real time making the patient the nexus point for managing the transition of care and building the care system around said patient. Patients are further challenged in a healthcare setting with managing much of their own care. This process leads to uninformed patients, mismanaged patients and a disjointed system. This type of mismanaged care leads to medical error, injury, unnecessary costs to the system, inefficient use of personnel to manage a poor system as well as myriad of other factors resulting in unnecessary costs. The costs can be related to personnel, hospital readmission, injuries, patient satisfaction which affects government reimbursement and has significant insurance implications. Thus, it is desirable to have a system where the patient is the center of the care and system is build around the patient driving information exchange, clear communication and expectations for the healthcare facility, patient and the family. Such a system would lower the risk of error and makes the process more efficient; allowing for seamless communication and information exchange during the transition of care.

Furthermore, improvements in living condition and advances in health care have resulted in a marked prolongation of life expectancy for elderly and disabled population. These individuals, a growing part of society, are dependent upon the delivery of home health and general care, which has its own set of challenges and drawbacks. Typically, home care is carried out either by the patient's family or by nonprofessional help. Even within a controlled facility the care management process is often mismanaged for this population. The monitoring equipment at home care facilities is usually minimal or non-existent due to the challenges associated with elderly and/or disabled populations, and the patient has to be transported to the doctor's office or other diagnostic facility to allow proper evaluation and treatment. A visiting nurse may perform about 1-2 home visits per stay. The visits have to be short and are usually not carried out on a daily basis. Moreover, a visiting nurse program usually provides no facilities for continuous monitoring of the patient and thus no care, except in fortuitous circumstances or in times of emergency.

In the home environment, proper identification and the ability to easily link to a patient to share personal data, diagnostic information and protected health information would likely result in more accurate and effective care. Currently, wristbands are removed as soon as a patient leaves the hospital (sometimes while still in the hospital) and tossed in the garbage creating a HIPPA security risk.

Therefore, there is a need for a secure, non-transferable patient identification system that when applied to the patient reliably identifies the individual regardless of their location, condition, age, size, and/or ailment which said device cannot be removed without permanently disabling the functionality both visually and electronically. There is also a need for a system that can offer critical information in real-time, making the patient the nexus point for managing the transition of care and builds the care system around the patient. Furthermore, there is a need for caregivers and sometimes the patients themselves to be able to access a system where important information can be securely sent to and received from medical providers.

SUMMARY OF THE INVENTION

This invention provides a method and system that can be used for at least one of information management, decision support, diagnosis and real-time communication before, during, and after transitions of care.

More specifically, a secure system and method to both identify a patient and provide access to relevant information such as the care team, help line, personal medical information, pharmaceutical details are disclosed. This information is preferably curated and designed specifically for each patient and can be customized to meet the needs of each patient. The customization will allow for data analytics and machine learning to find correlations between adverse events and other risk factors inside the facility, outside the facility, at home or in transition to another facility. In addition, the CID can serve as a link to telemedicine and other live support services. The inventive system and method reliably identifies the patient in any location and offers critical information or connectivity to personalized services such as telemed in real time making the patient the nexus point for managing the transition of care. The system and method are built around the patient by temporarily securely affixing a frangible nontransferable waterproof cutaneous information device (CID) to the patient's skin and then activating the CID by connecting it to a cloud based system. The frangible CID disintegrates when it is removed and thus cannot be transferred and is functionally inoperable when it is attempted to be removed. Therefore, even outside of a controlled environment a patient can be reliably identified and when the CID is removed, access to the system is closed and there is no further identification fraud risk to the patient. In addition, the functionality of CID varies based on the location. Inside of a controlled healthcare setting the access to patient information by the caregiver and the patient would be much more robust. However, once the patient leaves the facility, the software recognizes that the patient has left a controlled setting and adjusts the security to protocols to take this transition into consideration. This change of location can be done actively by connecting with the admission discharge program within the health system. This transition can also be identified passively by noting that the patient is no longer in range of the facility WIFI system or the GPS location of either the CID or the GPS location of the device interacting with the CID. By distinguishing between when a patient is in or around a facility and when they are not, Since the CID cannot be removed and is completely frangible, the device has created a way to create virtual frangibility by disabling the device based on location checkout procedures. In an alternative embodiment, the identification device can be remotely deactivated to render said identification device inoperable. In this case the CID, will demonstrate all the functionality of a physically frangible device but created via software. In addition, to the physical frangibility, whereby when the product is removed it is destroyed, the functionality of the device can be limited or ceased based on the variables unrelated to the physical state creating a "virtual frangibility" meaning no longer useful, making it defacto associated with a single user. By making the patient the nexus of care throughout the patient's transition of care, which could be long or short term, a facility or location which uses such a system would more likely properly transition the patient from one facility to the next location wherever it may be.

The inventive system includes a waterproof, temporary, frangible, nontransferable device bonded to the surface of the patient's skin so that a user can both reliably identify an individual and access information to administer care, administer care instructions and medical reminders/alarms, share protected health information or perform any other task related to the care of the patient which requires secure identification, regardless of where the patient is located.

Throughout the specification the term "transition of care" pertains to the transition of an individual and their associated care from one healthcare setting (origination point) to a destination (transitional destination). The transition can include but is not limited to Interdepartmental (e.g. Surgery to recovery, waiting room to surgical preparation, patient room to imaging, operating room to Intensive Care Unit, etc. . . . ) External Transfer (Hospital, Surgical or Emergency Room to Home, Assisted Living or Rehabilitation), or any other combination of transfers from one point to the next. This transition can also include a transition from one facility to the patient's home or temporary residence (e.g. family member's home). The transition of care includes not only the physical transfer of a patient from location to another but the continued update of the patient's medical or care data periodically or in preferably in real time to ensure that a service provider or caregiver is working with the most updated information possible, thus increasing the quality of care given.

The invention is a system and method to manage transition of patient care from one point to another point from a hospital using a temporarily cutaneous identification device ("CID") for identifying individuals in combination with a secure system of verifying the match of the patient and the device and access to information needed to manage or optimize care. Each CID is unique when it is created and cannot be replicated. The CID is frangible, nontransferable, unique, counterfeit-protected, water resistant identification device that is bonded to the skin, which provides a secure identification of the patient while at a given and location and before, during, and after any transition of care. In preferred embodiments, the device can also be rendered inoperable remotely. In accordance with one embodiment of the invention, the temporary cutaneous identification device includes a unique identifier by virtue of optical recognition or noncontact communication systems such as RFID, which may be read by any smart device, i.e. phone, tablet, reader or other similar smart device and connected to the inventive system to provide additional layers of security.

The CID may include a barcode datamatrix, QR code or other optical recognition protocols which may be read by a smart phone with an appropriate application which allows both 1) the input of data and 2) the retrieval of additional information either by direct request for keyword searching 3) extraction of physiologic data from the surface skin. This enables the generation of a more complete patient record at a central server.

In preferred embodiments, artificial intelligence software on a computing device with the capability of accessing the central server database periodically checks patient conditions, measurements, medications, and procedures and so forth to identify potential issues, inconsistencies, and other circumstances suitable for bringing to the attention of different types of medical personnel. Since the CID is applied to the actual persons body physiological data can be extracted using sensors, which can take readings from the surface of the skin. Medical diagnostic equipment can also interface with the CID to confirm identity before taking any measurements. The CID can virtually eliminate the risk of medical error as a result of misidentification regardless of location since the patient's CID is unique and nontransferable. The medical diagnostic equipment can take the reading and the CID and associated system can seamlessly and securely attach these data points to the patient record with no manual input or risk of human error. The CID serves as an input for artificial intelligence and machine learning software. By collecting data on the patient as they move from one location to another the CID system with the help of software can give visibility to the transition period. Thereby creating the ability to use data, machine learning and artificial intelligence to make key decisions which can improve the transition of care. One embodiment uses a blockchain to create a running ledger of the CID making counterfeiting extremely difficult.

The information is transmitted to the healthcare facility, either in an admitting area or on in a patient-care area (e.g., nurses station, emergency department, etc.). If the patient has an electronic medical record at the health care facility, a barcode, and/or a quadratic residue code or optically read code system, and/or an RFID microdot or microchip may be incorporated into the patient badge so that a link to more detailed information can be made immediately accessible using a reader device appropriate for the device or code. Thus, a secure code will link the patient to their associated data in the protected healthcare database. RFID and QR codes are currently used in healthcare but are often disjointed and designed for single systems. As a result, a bar code may only be compatible with one system and a second code may be needed for additional systems. This creates confusion and opportunities for error. Since each CID is unique and can be encoded with a unique identifier, healthcare systems can use the same identifier inside and outside of the healthcare facility. Healthcare providers can use this functionality to increase the level of care which patients can use this functionality to stay well informed in real time of their care management process even after they leave the hospital or other controlled healthcare facility.

A unique component of the system is the use of a skin wearable/embedded non-transferable, CID identification system to offer the needed level of safety and security related to the transition of care. The embedded authentication process ensures the security of the system. Specifically, patient security is insured, as the CID is non-transferrable, frangible and securely imbedded with a unique identifier the identity of an individual is unmistakable. This authenticated identification can be used to administer remote medical care solutions ("telemedicine'), remote care, monitoring or integration of any medical diagnostic device. Telemedicine and other remote monitoring systems are built on the premise that the correct individual is using the service but this is not always the case. Presently there is no system where secure identification bonded to the surface of the skin, applied a controlled setting where that same identification is used to transition and continue care regardless of the circumstances and location of the patient. The present system comprises having the CID applied in a controlled setting, such as a hospital admission department or authorized medical office. Once the device is properly applied to the correct person, any system interaction is secure as there will be no misidentification with a nontransferable CID. Put another way, once the CID is applied correctly to a particular patient, if the CID is read, the identity of that patient is un-mistakable since the CID can not be removed or transferred and the software functionality and access can be limited by time, location or other passive indicators.

Furthermore, in the case of a smart phone the authentication protocol is: The first point is the CID with is nontransferable with a completely unique noncontact communication device component, such as RFID; the second is a smart phone with fingerprint or secure authentication login. Once these two points are identified patients can access secure websites and portals without the need for logging in using a standard email and password identification. This process allows patients to skip the painful and cumbersome process of creating a password and remembering a password and during the transition of care, the most vulnerable time for a patient. An individual can automatically log into any personalized secure system with only a smart device and a CID. For embodiments with an RFID, the RFID connection will be severed if tampered. The secure patient ID system of the CID eliminates the cumbersome process of repeated entry of demographic and historic medical information eliminating human communication errors. Aside from a smart phone any number of devices can interact with the system using authentication protocols to verify that the device is authorized to connect to personal data, display protected health information or input new data.

For the unexpected transition (i.e. emergency), operators in the call centers or emergency response units get high quality information to identify patients that need urgent care so that they can be treated quickly, safely, and cost effectively. The could based tools allow easier access to patient information for authorized parties such as family members, neighbors, physicians, nurses, pharmacists, caregivers, and other affiliated parties to improved the quality of care for the patient. In the case of an emergency after a patient leaves a facility the CID can be used to provide Emergency Medical Services (EMS) staff with critical information at a time when these details could have huge impact on the outcome of the encounter. Since the CID, can be left on for days following treatment the patient can continually access information about their care and connect back to the hospital through traditional methods such as phone or text or through more advanced services like telemedicine. As a result, if an emergency happens and the person in question has a CID on the EMS staff can use a smartphone or other reader connected to the hospital system to pull up critical patient information about the patient. Aside from the hospital there are other systems in place for 911 calls where the calls are sent to a middleware system. This system pulls information from the Google™, Samsung™, Uber™ or any other application connected to the smart phone that made the call including GPS and shares that information with the EMS. If the call to 911 is triggered by a tap of the CID than when that call is received by the processing center and middleware the critical information from the healthcare facility can be linked thereby giving EMS access to the critical patient information without any further intervention. This is useful in any setting where a CID is applied and can be particularly useful where there is a staff member can trigger the initial call. Additionally, where the patient being treated is very young, elderly, and/or unresponsive, communication can be very difficult. The CID makes the critical flow of information possible.

In the home environment, proper identification could result in better care and the ability to easily link to a patient to share personal data and protected health information. Current wristbands are removed as soon as a patient leaves the hospital and tossed in the garbage creating a security risk. Conversely, the CID is inoperable when it is removed and cannot be transferred, therefore even outside of a controlled environment a patient can be reliably identified and when the CID is removed the system is closed and there is no further identification fraud risk to the patient.

BRIEF DESCRIPTION OF THE DRAWINGS

A more complete understanding of the present invention and the advantages thereof may be acquired by referring to the following description in consideration of the accompanying drawings, in which like reference numbers indicate like features, and wherein.

DETAILED DESCRIPTION OF THE INVENTION

There is provided a system and associated method comprising identifying and managing five components: Origination Point; Transitional Destination (which may or may not be a final destination); Patient with affixed CID; Cloud data management software, and Central and local server/processors.

Generally, in accordance with the invention, the inventive method (described in detail below) is initiated by a patient entering a facility for treatment and providing identifying information. The information is communicated to a central database/processor directly or via a local server/processor through, for example, a plurality of Internet connected computers, or, as illustrated, cellular smart devices (such as smartphones). Cellular smart devices are connected, via cell towers and cyberspace to a central server. The information is checked to verify if the patient is already registered in the system or if a new record needs to be created. Then the secure CID is applied to the surface of the skin. The CID in connection with authorized devices will be used to verify the identity of this individual. Access to the information contained on the central server will be managed by security protocols to ensure that the information being provided is on a need to know basis.

Figure 1:
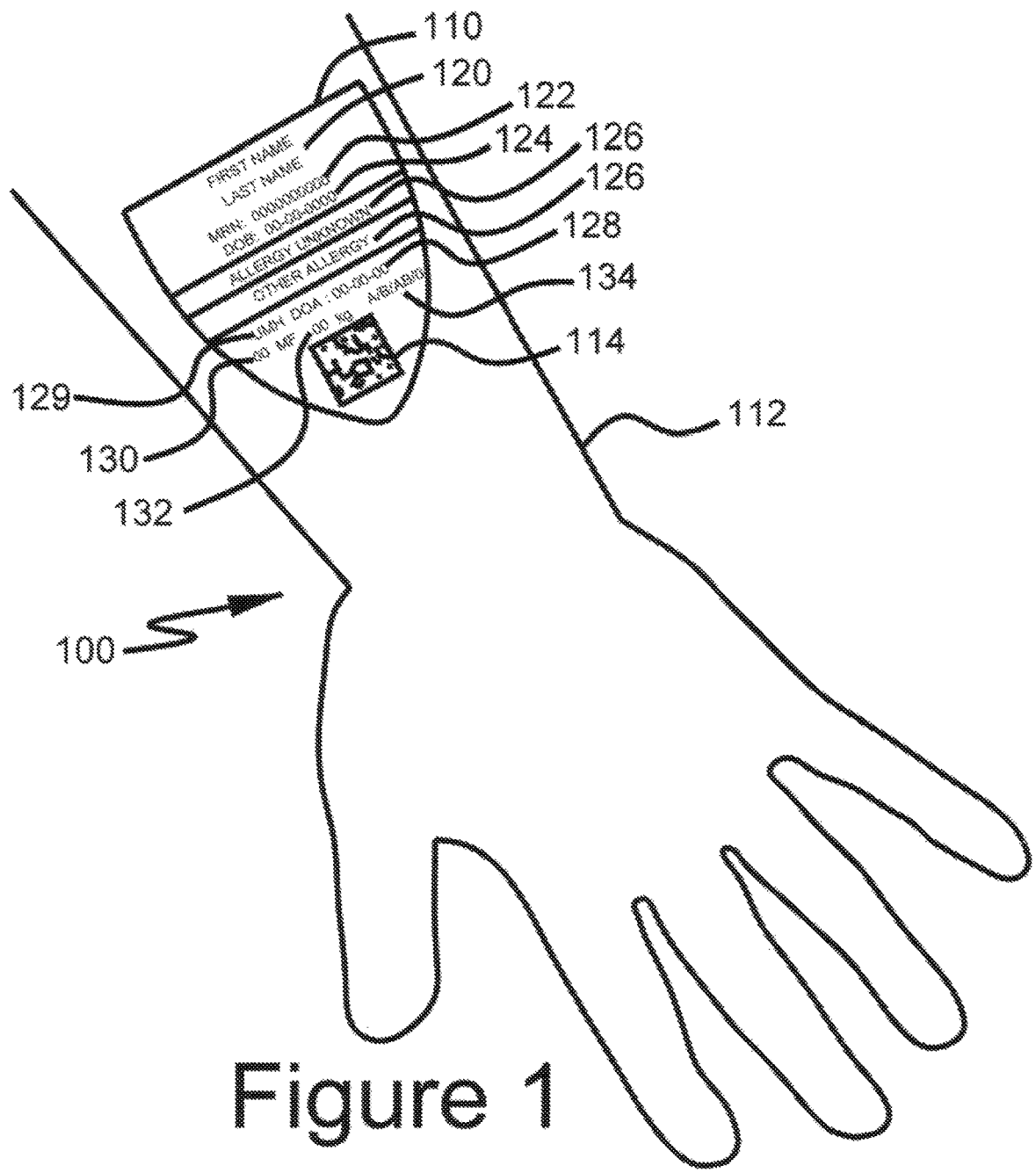
FIG. 1 shows a preferred embodiment of the CID applied to surface of the skin with detail on the visually displayed information located on the CID including an optically read code, which in this example is a datamatrix code.

FIG. 1 shows a preferred embodiment of a CID applied to surface of the skin with detail on the visually displayed information located on the CID including an optically read code, which in this example is a datamatrix code. CID 110 comprises ink and adhesive and would be printed on a printable substrate at the point of service. CID 110 applied to an individual's forearm 112. In accordance with the invention, it is contemplated that different sized patient badges may be used for larger and smaller people as well as varying application locations for the CID based on the environment. Likewise, it is contemplated that different sized patient badges will be used in different parts of the body. For example, a larger patient badge would be used on the chest of an individual while a relatively small patient badge might be used on the wrist. Other locations include the upper arm on adults and center chest on newborns. In the case of young children, the posterior may be appropriate. No intravenous devices are placed at those sites and they are readily visible, and have a large enough surface area. In a preferred embodiment CID 110 would be effectively tactically imperceptible so that it would not bother the wearer.

Upon arrival to the origination point, the individual is identified using CID 110 embedded with a two-dimensional code 114 such as a QR or data matrix code, other optical code system and/or an RFID chip or other noncontact communication device. Throughout the visit to the healthcare facility, the patient's records are stored on an electronic medical record system or patient data repository, i.e.) online patient portal. CID 110 will be used as the primary form of identification and also as part of the three-part identification system using verbal confirmation, visual confirmation of the CID with patient data and the electronic verification by reading CID 110 using a smart device. If all three match, then the individual is identified. Whenever there is any relevant interaction with the patient during treatment/care/management whether it is prescription drugs, wound care, bath, blood work, or any other interaction that requires identification of the patient, CID 110 will be scanned. A smart device with RFID or other non-contact communication capability can perform this function without any additional software. This software will allow an authorized smart device with optical or noncontact communication capability to read the CID whether using optical readers, RFID technology, Bluetooth or any other wireless technology available.

Figure 2:
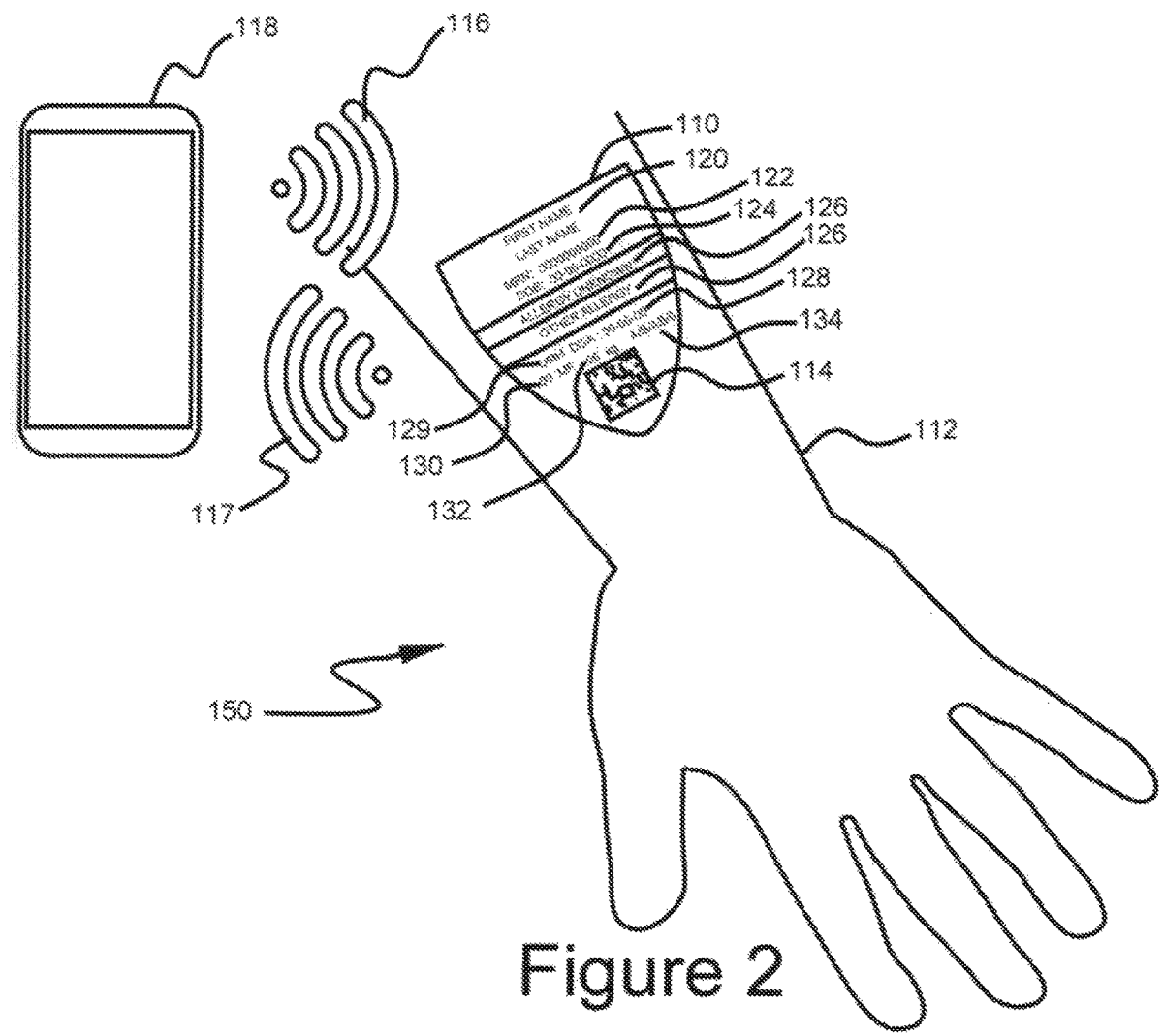
FIG. 2 shows the CID of FIG. 1 in noncontact communication with an authorized smart device.
Figure 3:
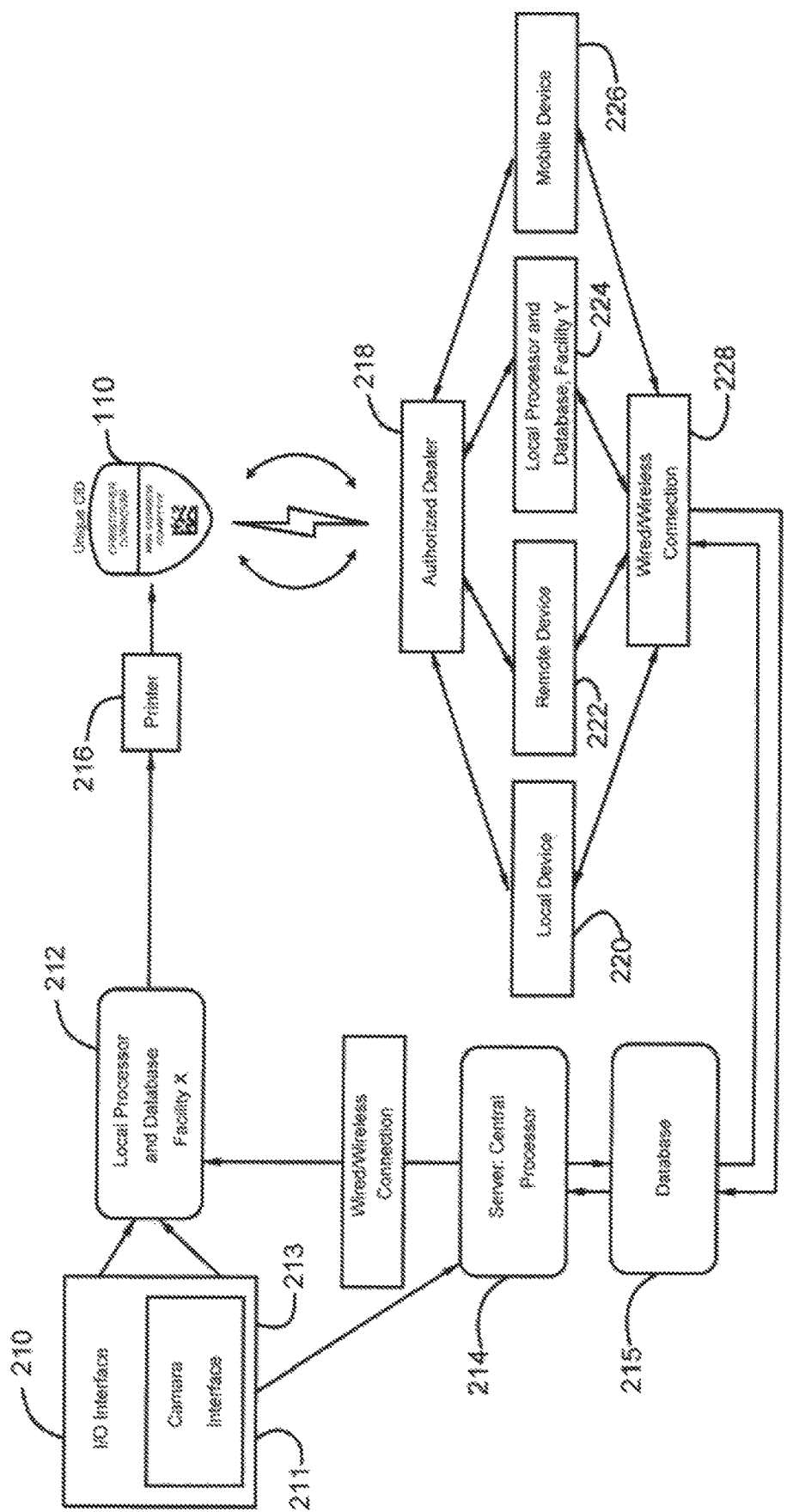
FIG. 3 shows a preferred embodiment of the system.

Referring to FIG. 2, an authenticated smart device 118 scans and reads code 114 on CID 110 located on the individual. This device can either be a specially built device or an internal use by a healthcare facility or a personal device used by the patient. If the patient uses the device the patient would have authenticated the device by normal methods of logging into their phone via fingerprint or alphanumeric code. CID 110 has a unique alphanumeric identifier 114 imbedded in the design. Referring to FIG. 3, alphanumeric code 114 is transferred to the smart device 118. Code 114 offers a level of security since the number has no value or use unless there is access to data management software located on the system's secure central server (described in detail below). Additionally, code 114 offers a reliable way to identify the patient. CID 110 further comprises additional information including first and last name 120, Medical Record number 122, DOB 124, notice of allergies 126, date of arrival 128 at facility that generated CID 110, location of printing facility 129 and may include additional information such as gender 130, weight at time of check in 132, blood type 134. For a patient, by using an authenticated smart device as well as standard fingerprint or other unique and nontransferable authentication protocols which may be embedded in the device in conjunction with CID 110, a user can automatically authenticate and log directly into any application, native or web-based, which contains any level of secure, personal and or sensitive information thus bypassing the sometimes painful registration, sign-up process. Referring to FIG. 1, each patient badge 110 includes the name 120 of the patient, and the patient's date of birth 124. A patient ID number 122 also appears on CID 110. In the example given in FIG. 20, allergies are indicated at position 126. In this case the letters "PCN" indicate a penicillin allergy. While the embodiment shown includes optically readable code 114, it is understood that any automated readable device, such as an RFID chip, a quad code, and so forth, may replace optically readable code 114. Moreover, it is noted that the system may accommodate OCR capability, which would make the generation of a machine-readable code, such as code 114, unnecessary, because the system could simply read the same information that a human operator reads but unlike a human reader, the system would process the information to provide an authorized device and user to access additional information which is not seen on CID 110.

A hardware system constructed in accordance with the present invention and suitable for practicing the method of the present invention is illustrated in FIG. 3 with CID 110 as the nexus point of the system with servers and other devices communicating via CID 110 to administer care input and share critical information. System 200 comprises input/output interface 210. I/O interface 210 could for example be a smart device, computer, etc. and would have the capability of to receive human input of identifying information. Interface 210 may be linked via wired, wireless, Bluetooth, local processor/database 212, which is linked via wired or wireless connection 213 to central server 214. In an alternative embodiment, interface 210 directly connects to central server 214. Local processor/database 212 is connected to printer 216, which is capable of printing CID 110. CID 110 may interact with an authorized reader 218. Authorized reader 218 is a device that is used to interact with CID 110. Reader 218 can be connected with a local device 220 such as a within facility glucose monitor, medical diagnostic equipment, radiology equipment and the like, or a remotely connected device 222 (e.g. home medical diagnostic equipment); facility Y server 224 (e.g. a server at a second facility), mobile device 226 (e.g. smart device that is not tethered or bound by location or individual or equipment) all of which are connected via wired or wireless connection 228 back to central server 214. Authorized reader 218 can be incorporated directly into devices 220-226 or can be an external stand-alone reader. Central server 214 communicates with system 200 inputs via interface 210. Central server 214 comprises a database. Central server 214 also provides the database with patient badge design information generated by a patient badge design algorithm, which may be accessed, by central server 214. Such patient badge design information is also stored in the database, which may be a hard drive, solid-state hard drive, or any other suitable storage medium, device, integrated sub system, and so forth.

Authorized reader 218 also allows a connected device to communicate with central server 214 for the presentation of data input screens, audio alarms, and the transmission of data to the central server 214. Reader 218 can be a non-contact communication device such as RFID or can be an optically read code (QR, bar, etc.) read by an optical code such as a camera or a red laser scanner. Reader 218 is input and output device, which would allow a large number of mobile devices such as mobile device 226 to communicate with central server 214. In the case of smart mobile devices, such functionality is typically incorporated thought there can also be a separate stand-alone reader (e.g. a mobile scanner) for devices, which do not include this function.

I/O interface 210 preferably includes a camera 211, which may be used to take a picture of the face of the patient, for example at the time of patient intake. Such picture is advantageously taken before information received from the patient is entered into the system, and before doctor/healthcare worker inputs into the system. Such picture is then advantageously displayed on the information input device during information entry to reduce the possibility of error due to misidentification of patient during data entry. Advantageously, the picture of the patient and/or patient name optionally remains on the screen in a fixed position as information is input into the system, for example on a personal computer or mobile device, for example a mobile device with a touch screen (such as a smartphone with an application enabling the inventive system).

In accordance with the invention, it is contemplated that the patient admission area (or at bedside) of the health facility will have on hand a number of input devices such as input device 210, which may take the form of a mini tablet, or full-size tablet incorporating a camera and connection (wired or preferably wireless) located in the admission area. Depending on the admission circumstances, when a patient is being admitted, an input device 210 may be given to the patient. The input device prompts the patient to fill in various informational units to be used by the system. The central server 214 directly transfers this information, including an image of the face of the patient, which is stored in the central server and shared via the wired or non-wired connection 213 with local server 212.

In accordance with the preferred embodiment, it is contemplated that a patient may take his/her own picture using input device 210. Alternatively, a nurse may use the input device 210 to take the picture of the patient, as that is likely to ensure image quality and uniformity of presentation. In connection with the taking of the image of the patient, the display on input device 210 may include a rectangle within which the face of the patient should fit. This will assure uniformity of presentation, maximum information by maximizing the size of the face of the patient, and reduce the time necessary to compose the picture. While the above system in a hospital setting, it is understood that initial input device 210 may be in a number of settings including a primary facility or any other authorized facility connected to central server 214.

Figure 4A:
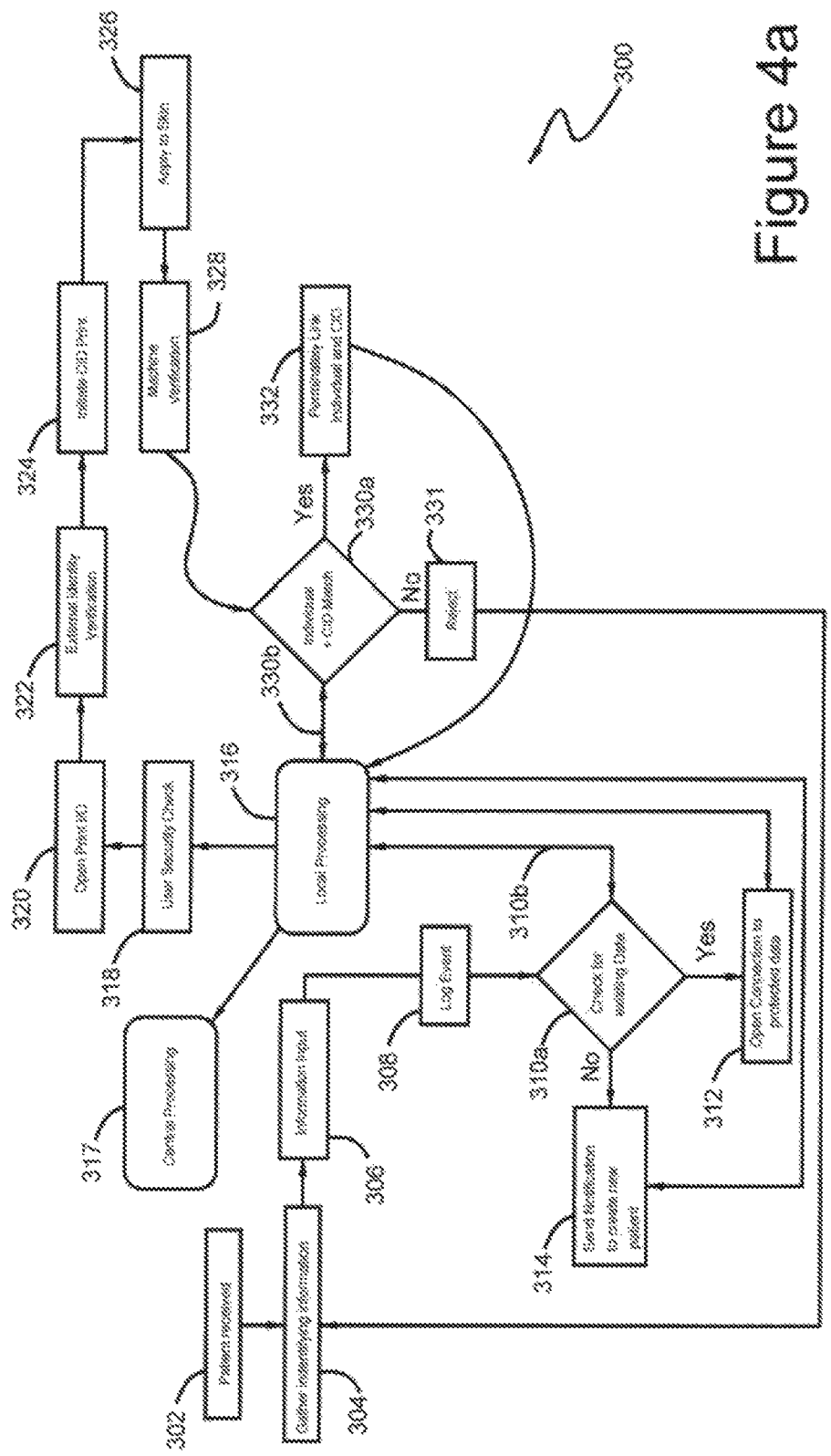
FIG. 4*a* is shows a preferred embodiment the inventive process utilizing the system of FIG. 3.
Figure 4B:
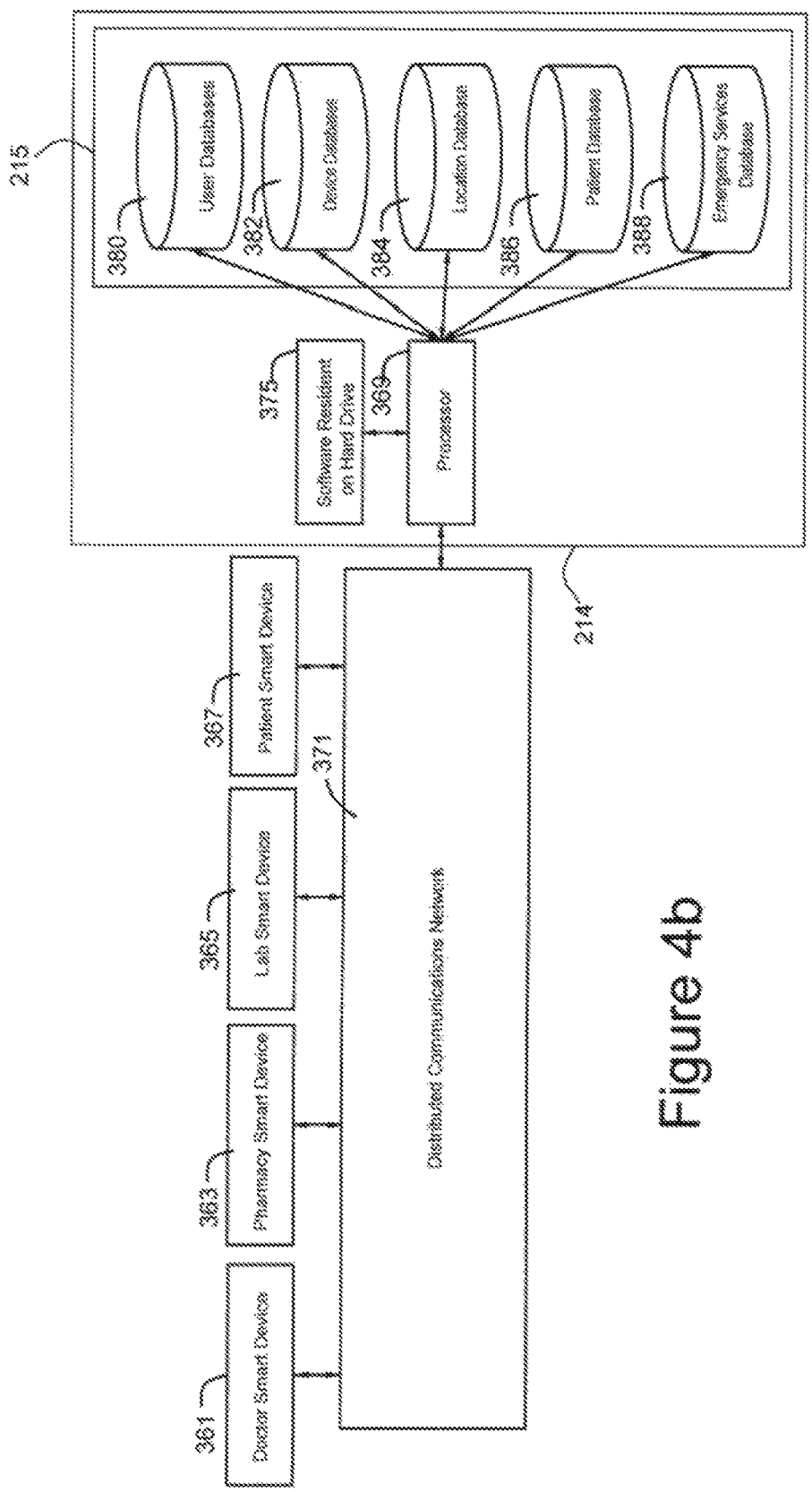
FIG. 4*b* is a preferred embodiment of the process of FIG. 4*a* with several users managing a patient.

A method of the present invention is illustrated in FIGS. 4a and 4b. Method 300 describes the initial generation and authentication of CID 110. Initially, a patient is received at step 302. Then identifying information (such as Name, date of birth, medical record number, government identification number) is gathered from the patient at step 304. In accordance with the invention, CID 110 may comprise a selection of information taken from information gathered at step 304. As the information about the patient is gathered and sent to the central database, revised patient badges may be generated using the same protocols used in method 300. Information is input at step 306 via I/O interface 210. Then the information is sent via wired or wireless connection, to central server 214 to log the event at step 308. Then at step 310, central server 214 checks to see if there is an existing record. If there is an existing record, then at step 312, connection is opened to the protected data and is retrieved and if there is not an existing record, then at step 314 a new record will be created as described in detail below. Once a record is retrieved or newly created, at step 316, the information is sent to the local computer 212. Then at step 318, device 212 performs a user security check via any number of protocols mating the patient with the medical record number through the EMR, using a cloud-based audit system to verify the authenticity of he CID and matching the device to an authorized user. Then, at step 320, interface 210 displays information and then at step 322, there is an external identity verification, which could include a number of known protocols including biometric or password protocols. Then at step 324, directions are sent to the printer 216 to print CID 110.

The device can be made frangible in various ways. In preferred embodiments, this is done by perforating the substrate if removal is attempted the device will rip apart and therefore rendered nonfunctional and destroyed. If removal is attempted with acetone the device will also be destroyed. Due to these attributes, the device is nontransferable. Also, in some preferred embodiments, the strength of the adhesive will exceed tensile strength of the substrate making it impossible to remove the shield in a single piece. Additionally, an RFID can be printed in metallic ink making it impossible to remove in one piece and could have various weak points on the antenna, the connection of the antenna to the integrated circuit or the integrated circuit itself not allowing the antenna to be removed in one piece with the integrated circuit attached.

As discussed above, CID 110 comprises an adhesive layer, and may comprise RFID or other non-contact communication device, flexible circuitry, substrate layer of varying thickness depending on the application and ink applied layer which contains individual specific information which can be visually seen or read including the use of bar, data matrix, QR or other optical code system. After application, the result is a visually read optical display comprised of ink bonded to the skin by the adhesive with a noncontact communication device such as RFID imbedded into the device. Accordingly, after patient badges are generated at step 324, the patient badge design generated by the system at step 410 (see FIG. 5) the patient badges are applied to the patient at step 326. Then, at step 328 an authorized smart device reader scans CID 110 and sends the information to device 212. Then, at step 330 local processor 212 checks to confirm that CID 110 and the individual match. If there is a match, then at step 332, CID 110 and the individual record are permanently linked and the event would be logged at central server 214 either directly or via local device 212. If there is a rejection, then at step 331, the system 200 returns to step 304 to gather more identifying information.

Referring to FIG. 4b, a typical execution of the inventive method involving a plurality of authorized users 361, 363, 365, and 367 for a single patient is shown. For example, user 361 may be a doctor, user 363 may be a pharmacy, user 365 may be a lab, and user 367 may be the patient. Each user would use an authorized reader 218 to first log into system 200 and connect to central server 214, via a distributed communications network 371, such as the Internet. As discussed above, authorized reader 218 may be smart devices or personal computers or any other suitable computing and/or communications device, a scanner connected to a local server (e.g. hospital scanners) which is connected to central server 214, using services provided by the respective user's Internet service providers. Typically, an authorized reader 218 would include software, such as an app that is preinstalled or authorized users would have downloaded in advance to pre-authorize the reader. Whenever a user wants to log in to system 200 to send or retrieve information, access is determined by is controlled by software resident hard drive 375 and the processor 369 in central server 214 by checking the appropriate one of a plurality of databases 215 which comprises a series of databases, namely authorized user database 380, authorized reader database 382, authorized facility database 384, authorized patient database 386, and emergency personnel database 388.

Whenever an authorized user wanted to access database 215, initially the first layer of authorization would be provided by checking authorized user database 380. Then the authorized reader being used to send the request for access would be checked against authorized reader database 382. For certain tasks and during a medical facility stay, staff (e.g. nurses) may carry around scanners that are specifically tied to their particular local server, which would be entered into authorized facility database 384. Once the identity of the user is verified, then it is cross checked with the authorized patient database 386 to determine if indeed the user is authorized to access this particular patient's information and depending on the information in database 380. For emergency personnel, there can be provided a limited access emergency personnel database 388. The combination of databases, security protocols and smart software and processing allows for the seamless transfer of information and instructions.

For example, patient's doctor sends through device 361 sends a lab order to the lab device 365 and the system 200 sends a note to the patient's device 367 to go the lab. The patient gets the lab work done and goes home. The lab via lab device 365 sends to the doctor device 361 the results via central server 214 where database 215 is updated with the latest results. Doctor sees on device 361 the results then sends a prescription to the patient's pharmacy device 363 and the system automatically generates a message to the patient's device 367 regarding the new prescription. Meanwhile, the patient falls and needs an ambulance. The emergency personnel scans the CID 110 and a notification via central server 214 is sent out to the doctor device 361 and pharmacy device 363 that the patient is en route to the hospital and central server 214 sends the pharmacy orders to the hospital. Alarms and other notifications may be set up in central server 214 to send reminders for follow up post discharge. The seamless transfer of information is facilitated by the patient wearing CID 110 so that the patient is always securely identified and the center of care and access to information.

Figure 5:
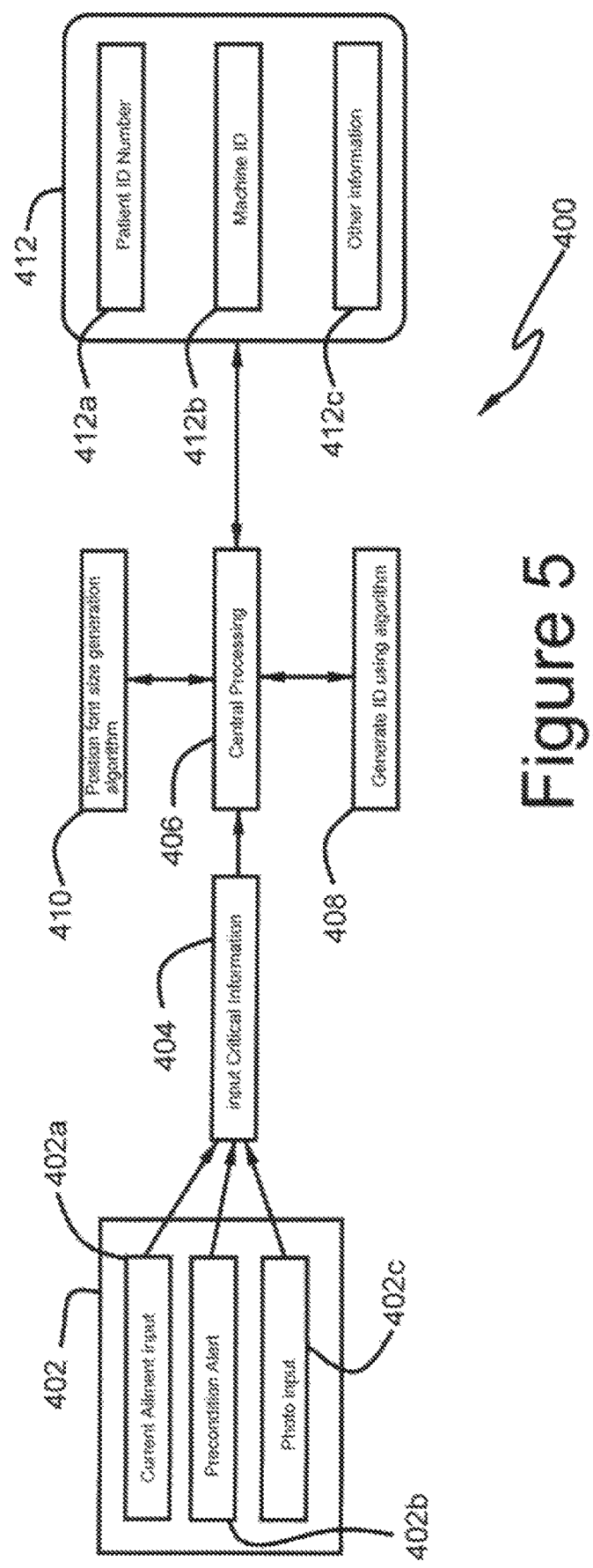
FIG. 5 shows a preferred embodiment of the intake process of FIG. 4*a*.

FIG. 5 shows, in greater detail, a new record creation step 314. At step 402 for an expedited intake process, the critical information is gathered that is needed to generate CID 110. Such information may include current ailment input 402a, pre-condition alert (including allergies) 402b, photo 402c. At step 404, the critical information is input. Then at step 406 the information is sent to the central processor 214 for storage and processing. Then at step 408, a new patient ID number is generated using a machine ID generation algorithm. Then at step 410 an algorithm is used to determine position, font, size to decide the positioning of the printing.

After basic information has been gathered from the patient and stored in the appropriate database, either immediately or at a subsequent appropriate point, the patient badge design is sent to printer 216. In accordance with the invention, at step 412, central server 214 also generates an identification number and machine-readable identification, such as a barcode, using a generation algorithm. In an alternative embodiment, the identifying number could be the unique code pre-populated on an RFID chip or like device. As described above, this information and other information input into the system is used by central server 214 to generate a patient badge design which is stored, along with other information in central server 214.

Figure 6:
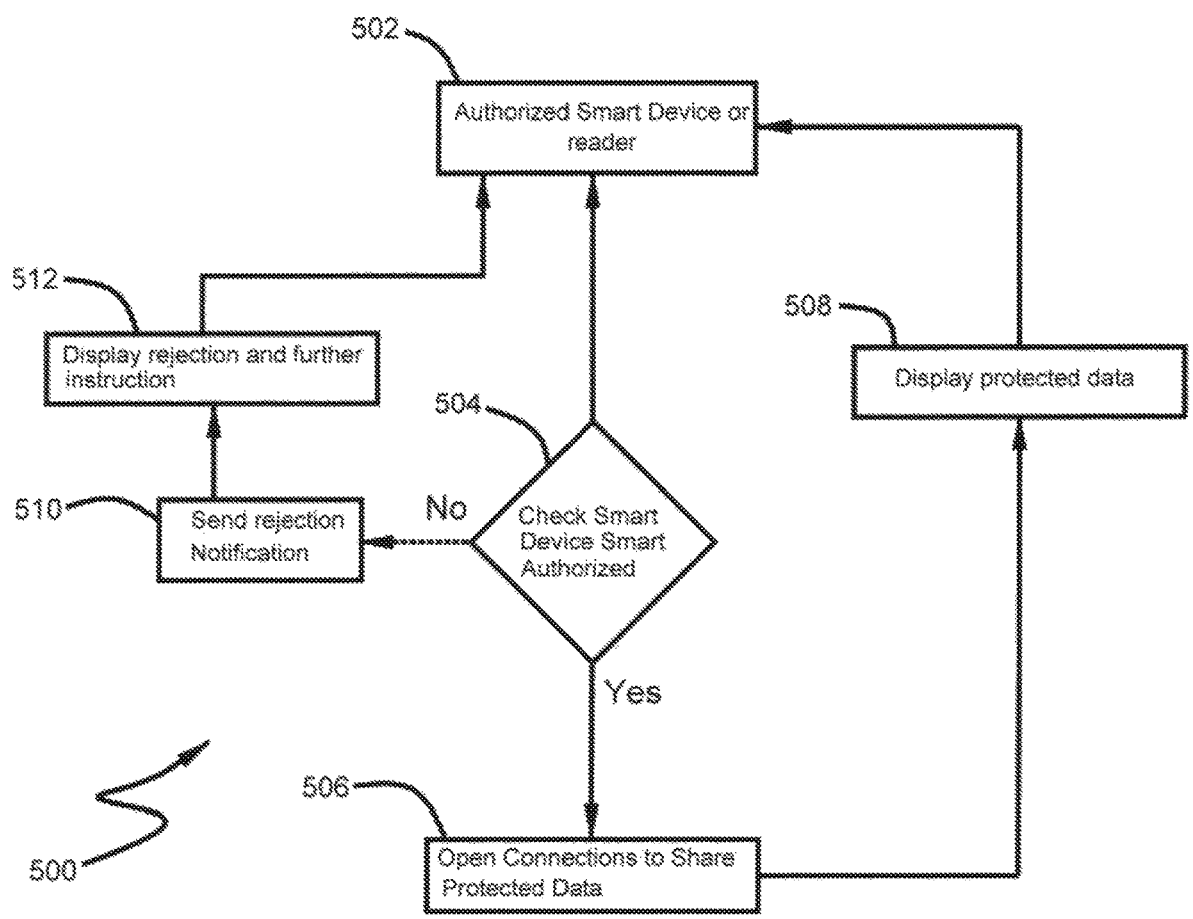
FIG. 6 shows a preferred embodiment of the authentication process of FIG. 4*a*.

After device 110 is connected to central server 214, FIG. 6 shows how an authorized device, either local or remote, attempts to interact with CID 110 at step 502. Then, at step 504, there is a check to confirm that the device is authorized. If yes, then at step 506 a connection is opened to share protected data, then at step 508 interface 218 displays an interactive screen to access protected data. If no, then at step 510 central server 214 sends a rejection notification to the non-authorized device and at step 512, rejection is displayed on interface 218 and further instructions are given. In accordance with the invention, it is also contemplated that additional information in step 404 may be gathered at the point of admission or shortly thereafter, such as patient height, weight, blood pressure, and so forth. Such information is also stored in the database for subsequent updating and retrieval. Likewise, existing information in the database of the hospital may be automatically retrieved at the time of patient admission and, where appropriate the information may be presented for patient verification.

After device 110 is connected to central server 214, FIG. 6 shows how an authorized device either local or remote attempts to interact with the CID 110 at step 502. Then, at step 504, there is a check to confirm that the device is authorized. If yes, then at step 506 a connection is opened to share protected data, then at step 508 interface 218 displays an interactive screen to access protected data. If no, then at step 510 central server 214 sends a rejection notification to the non-authorized device and at step 512, rejection is displayed on interface 218 and further instructions are given.

Figure 7:
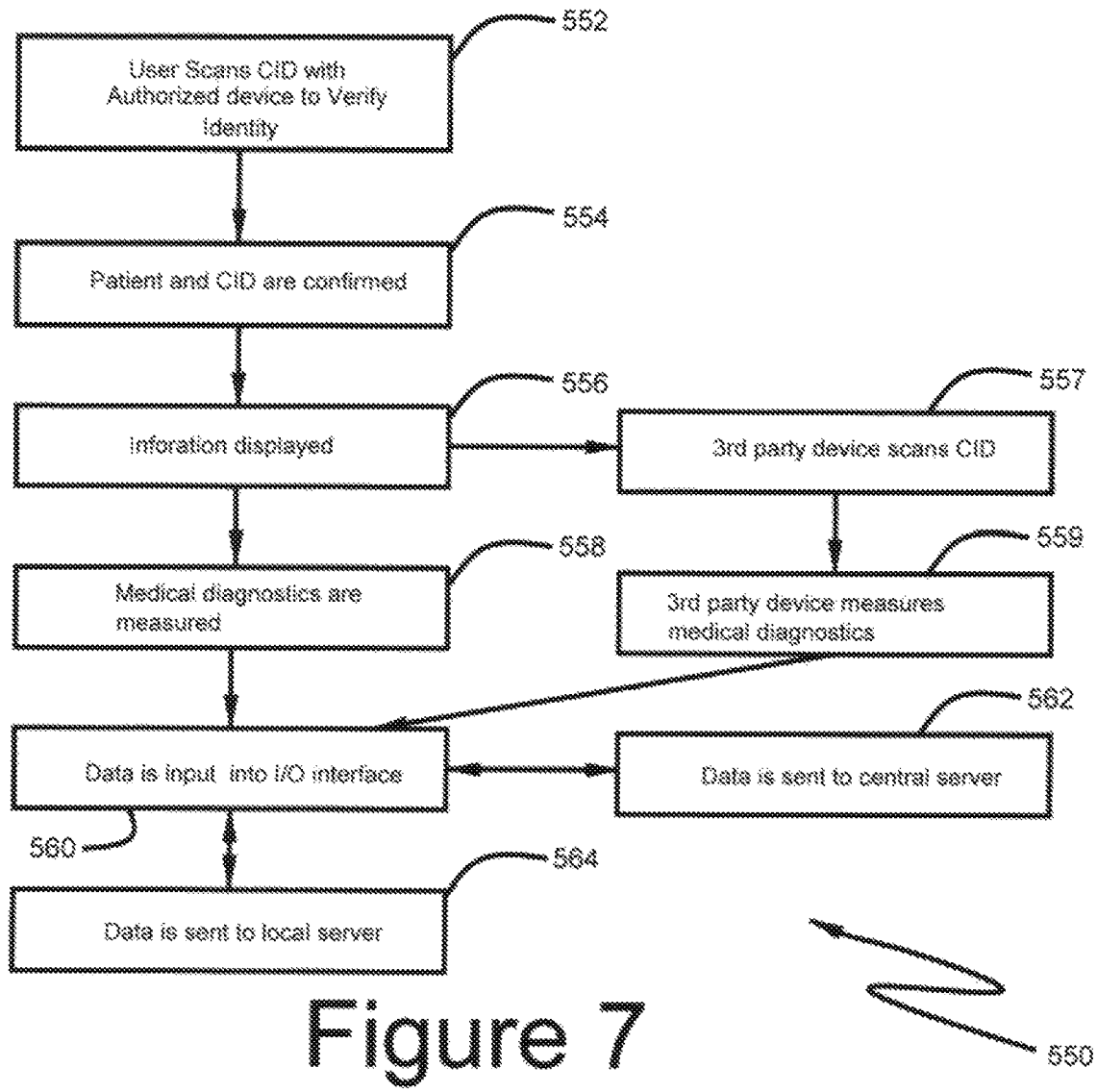
FIG. 7 shows a preferred embodiment of the medical information input process of FIG. 4*a*.

In accordance with the invention, CID 110 may be applied to the patient as more fully appears and as previously disclosed. FIG. 7 further describes an interaction with a CID with in a facility for the purposes of collecting data and administering care. In step 552, CID 110 interacts with an authorized device to verify identity of the patient. In step 554 the identity is verified using the process described in FIG. 6. In step 556, information and data related to the patient is displayed. In step 558, medical diagnostics are measured on devices that are not connected or lack the ability to scan CID 110 such as a thermometer. In step 562, the data is input into the I/O interface 210 corresponding to the patients scanned in step 552. In step 557, a third-party device scans CID 110 to link subsequent diagnostic measurement to the patient such as a glucose monitor. In step 559 the 3rd party device measures the medical diagnostics. Similarly, as the process in steps 556, 558, 562 above, in step 562, the data is input into the I/O interface corresponding to the patients scanned in step 552. In step 564 the data is sent to the local server. In step 566 the data is sent to the central server. In a non-medical facility setting, the information may be input by the caregiver.

After the initial stay at the origination point, the individual in a healthcare setting is now comfortable using the smart device throughout the stay and the habit has been created to scan CID 110 when information is needed or relevant information is gathered. When the individual is discharged from the facility, CID 110 becomes the lasting link between the patient and their subsequent care. At the origination point CID 110 is applied and the patient begins the habit of using CID 110 as described above to continuously or periodically update the EMR. When the patient is transferred to the next destination, CID 110 becomes the nexus point allowing the patient or caregiver to obtain information from CID 110 regarding any number of critical factors including time, location, instructions, previous notes, test results, scans, or any other possible data that can be extracted from the central database 214 using CID 110.

Figure 8:
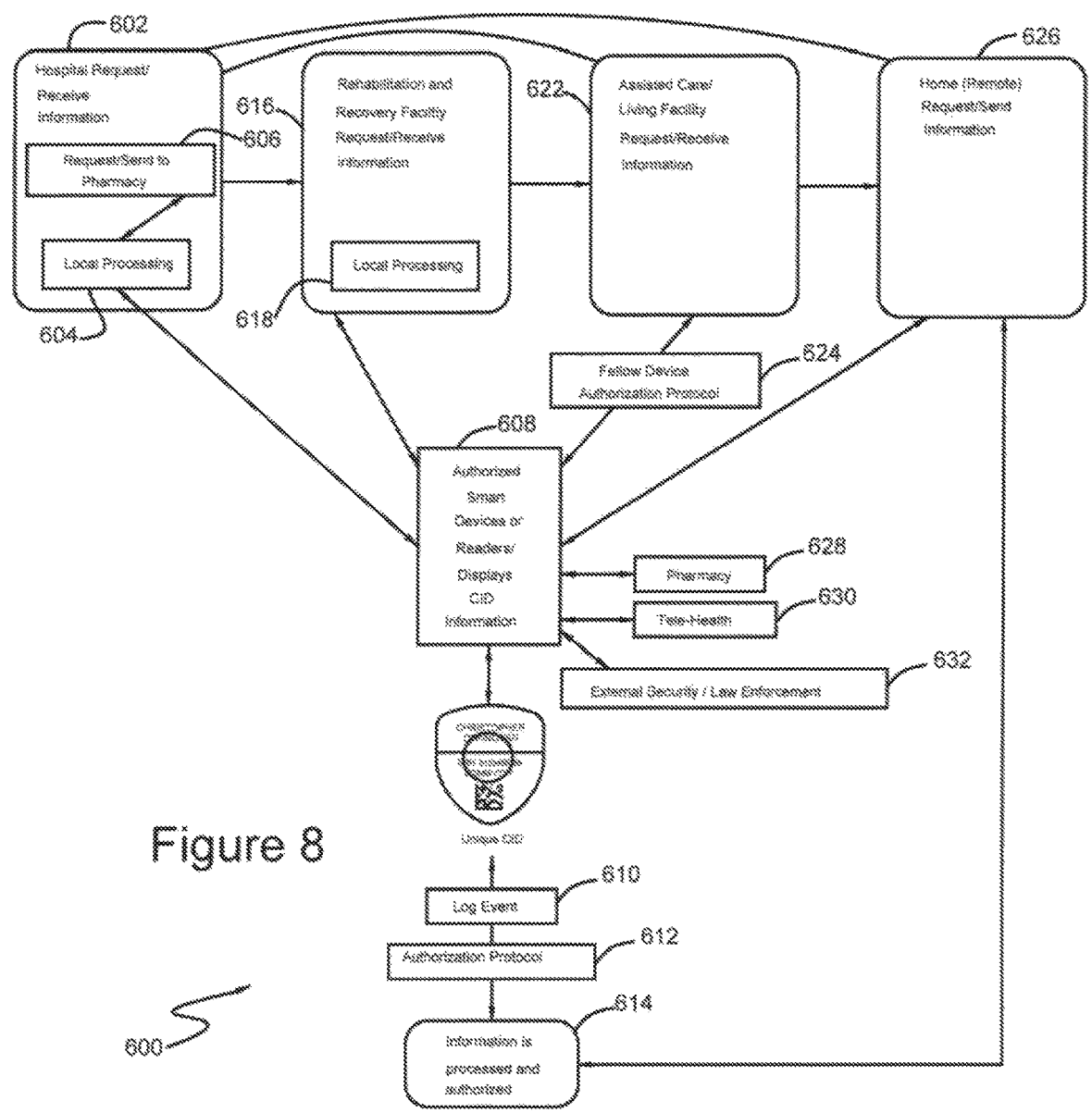
FIG. 8 is a preferred embodiment of the transition of care process from one facility to a different facility using the CID as a nexus point.

FIG. 8 shows the interaction and coordination of the information through the combination of the central server, CID, and authorized devices once CID 110 is paired to the patient. Referring to FIG. 8, at step 602, an authorized smart device 218 requests information by interacting with the paired CID 110. While the patient is at the hospital, addition information will be gathered to fill in and update the patient record using CID 110 as the nexus point. Throughout the patient's hospital stay, there will be treatment and diagnostics and the like, where CID 110 will be scanned with an authorized device and the information will be sent to the central server as seen in FIG. 7. All of those events will be logged events. Furthermore, it is anticipated that within the hospital there will be devices such as diagnostic and monitoring equipment as well as other facilities, departments including phlebotomy, radiology pharmacy which could already be connected either directly to the central server or via the local server 212. For example, after an examination, at step 604, local server 212 processes information from within the hospital gathered through authorized devices (e.g. remotely connected glucose monitor) and then updates the database in central server 214. System 200 is particularly advantageous when used in connection with medication orders sent to the hospital pharmacy. When an order is put into the pharmacy, and the medication is received, CID 110 and medication will be scanned and then the patient will be given the medication. At step 606 a request is sent to the hospital pharmacy to confirm that the right medication went to right patient. This is in stark contrast to prior art systems where a static barcode on a wristband can be replicated or old ones are thrown in the trash. The current system relies on check digits, a form of redundancy check used for error detection on identification numbers, such as bank account numbers, which are used in an application where they will at least sometimes be input manually. It is analogous to a binary parity bit used to check for errors in computer-generated data. The suffix or prefix digits are used to distinguish between the wristband and a label used, for example, for a prescription. This is an extremely low bar for security requiring only cursory knowledge of barcodes to easily hack the system. Furthermore, in the prior art systems staff could technically perform these checks without physically being in front of the patient. The present system with a CID—must be physically with the patient where the patient and CID 110 are effectively one and the same.

Following stabilization of their acute medical issues, a patient's hospital treatment is finished. Before the patient is sent home, he or she may be sent to an Inpatient Rehabilitation Facility. These are typically free-standing rehabilitation hospitals and rehabilitation units in acute care hospitals. They provide an intensive rehabilitation program. Rehabilitation facilities were created to meet a perceived need for facilities which were less costly on a per diem basis than general hospitals but which provided a higher level of professional therapies such as speech therapy, occupational therapy, and physical therapy than can be obtained in a "skilled nursing care" facility. A rehabilitation facility is usually accessed following a stay as an inpatient if the hospital team determines the patient will benefit from rehabilitation services. A report concerning the patient's needs will be sent to the rehabilitation hospital, as well as perhaps some of his/her medical records and a recommended treatment plan. Some of this information is usually but not always transmitted with the patient. This transition of care from one facility to another facility often results in multiple undesirable issues associated with the hand off from one location to another as well the subsequent care for the patient at the new facility. Oftentimes the documents are not available and there are unnecessary delays related to managing the intake process at the new facility. This process can be cumbersome, time consuming and wasteful as staff is double efforts to makeup for the system inefficiencies while the patient suffers and the staff underperforms due to a poorly designed system. In contrast to prior art systems, CID 110 makes the patient the nexus point to gather information about the patient, instructions for medication and treatment is managed through a central server 214 and the patient (or their authorized medical proxy) is the key to allowing access to that information. The patient is at the center of his or her own care with a device that could not have been applied to the skin unless done in a controlled setting and could not be removed or transferred without being destroyed. Therefore, when the patient, service provider or caregiver needs relevant information either for themselves, family or the caregivers, all that is needed is a patient with CID 110, and authorized interface 218 connected to central server 214 to allow care to continue seamlessly and efficiently with no interruption or negative affect on care management.

Referring again to FIG. 8, if a patient is discharged to an Intermediate Rehabilitation Facility, when the patient arrives at the new facility, CID 110 is scanned by authorized reader 218 and communicates to the central processor to confirm location and authenticity of the device paired with CID 110. Facility personnel or caregivers at the receiving facility (depending on the setting) will first authorize or confirm authorization of a smart device as described in FIG. 7. The receiving facility will at step 608 first scan CID 110 with an authorized reader 218. At step 610, device 218 will send a log event notification to central server 214. At step 612 smart device 218 also sends an authorization code to a secure server (as described above). The information is processed at step 614 and then sent back to local server 224. From that point on every time any relevant information is gathered at that facility, CID 110 is scanned by an authorized smart device and as described above in FIG. 7, the database in central server 214 is more or less updated in real time or periodically allowing for accurate treatment and judgment of patient's needs. Additionally, the access to the central server 214 allows for quick recall of any information that is not in the local system 212. CID 110 is always married to the patient and CID 110 in conjunction with authorized interface 218 and central server 214 manages any logged interaction between the patient wearing CID 110 and the facility. This interaction starts with the verification of identity. Once this identity is confirmed using the nontransferable frangible secure CID 110, which is bonded to the patient one, cannot build on that foundation to perform any number of secure tasks that require reliable secure identification before proceeding. Once this connection is in place information can be send and received about the patient. This information can be directly related to the care of the patient, patient management or can be used to relay other information regarding the patient which would be considered personal and could be protected by government (e.g. HIPPA) guidelines. This connection between the patient and the system in place by utilizing CID 110 can also allow for the recording medical diagnostics and other health related measurements, which are critical to the safe care of the patient. This information is often the basis of patient care and decisions such as medication dosages. Such medical decisions can have grave consequences including death caused by medical error. In prior art systems, the staff is tasked with managing the weight glucose level and other measurements manually by taking the reading and writing down the number or memorizing the number as one walks from the scale to the bed for example. This manual process forces medical staff to create workarounds to facilitate the work that needs to be done. In some facilities, stickers are placed on the arm of staff members. As staff members take reading and measurements, the sticker on the arm, which is identical to the patient wristband, is scanned in lieu of the actual performing the action in front of the patient. This creates multiple opportunities for error. The present inventive system comprising CID 110 that can not be duplicated so all reading must be taken in front of the patient forcing medical staff to focus on the patient directly and eliminate the possibility of workarounds that are possible with a wristband.

This data, information and measurement taken are updated in local and central databases, with the central server sending notices (alarms, notices, follow up reminders and check-ins and the like), thus and putting in a process in place to keeping the patient (and/or their designated caregiver) educated and well informed about patient care regardless of where the patient is physically located during the interaction. This is in contrast to prior art systems where hospital wristbands are used which track the band not the patient and can be easily copied (or found discarded in the trash), or bar code systems where staff scan stickers corresponding to the patient and do not need to be physically in front of the patient to perform these activities. Furthermore, an RFID system alone, merely verifies the existence of the band not necessarily the patient. Alternatively, when the patient is outside of the hospital no identification is available and patients use log in and password systems to verify identity outside of the hospital.

A patient may be discharged to a facility such a nursing home; an assisted living facility; or group home. A nursing home is typically a private institution providing residential accommodations with health care, especially for elderly people. There are also nursing home alternatives/alternative care facilities for persons who are at risk of living alone but do not require nursing care. A group home is a private residence for children or young people who cannot live with their families, people with chronic disabilities who may be adults or seniors, or people with dementia.

If a patient is discharged to the care of such a facility at step 622, the caregiver/responsible receiver first scans CID 110 with an authorized smart device 218 and then at step 624 authorization protocols of FIG. 7 are implemented. Similar to protocols as described above for rehab, if the smart device of the caregiver is not authorized, then device authorization protocols will need to be implemented to authorize the device. Once the new smart device and CID are paired, then relevant information will be logged scanning CID 110 and the relevant information will be sent to central server at step 614, device 218 will send a log event notification to central server 214. At step 612 smart device 218 also sends authorization code to a secure server. As shown in FIG. 8 when a patient is discharged for a long or short term to a non-home setting, there is often the inconsistency of staff and errors in care often occur due to human communication and limited staff resources. The inventive system is particularly useful by making the patient the center of all communications. As discussed above, all relevant information is input by scanning CID 110 and with an authorized device. Such information can be sent via local computer or directly to central server 214.

Prior art systems that deal with care at home put processes in place to manage each individual system and authenticate the system using biometrics or password log in process. These systems each perform a different task and each find ways to log the patient in to perform the task. When the patient is out of sight, healthcare facilities cannot use the wristband and rely on log in and other authentication methods to manage the home care and rely on caregiver management to fill in communication gaps. However, it is unrealistic that someone could manage all of the disparate systems without a central management system and often results in error. These issues are addressed by the present inventive system, which allows for an identification device that was applied in a control setting to link the patient back to the facility where care was initiated to manage the process that needs to take place outside of the hospital. Each home monitor or device would be preprogrammed to initiate with CID 110 and the connection to the patient would be guaranteed and secure. During the time when a patient first arrives at home is the most dangerous time for a person in need of care. The vast majority of readmissions happen just a few days after discharge and this is directly related to avoidable mismanagement, an event that would not have occurred with good home care management. With the present invention, for the patient managing care at home is as simple as wearing a CID. Since CID 110 is linked back to the central database, the care can be managed using algorithms, reminders, alarms and warnings. And can link the care from OP to TD in this case home in a way that is simple, reliable and secure. Patients can be cared for seamlessly at home connecting all the disparate systems using one simple device thereby increasing compliance, reducing avoidable readmissions, raising the level of care and increasing the satisfaction of the patient experience.

Regardless of where the patient is, authorized interface 218 using protocol 608, can also be connected to an external pharmacy system 628, remote health services 630, and an external security law enforcement at 632. Alternatively, while at the facility, users may be given option to sign onto the wireless networking system for the facility, and thus avoid use of their cellular time and data. In the event that the user is on the facility's private wireless network, the private wireless network of the facility may also be used to determine the location of the user.

Figure 9:
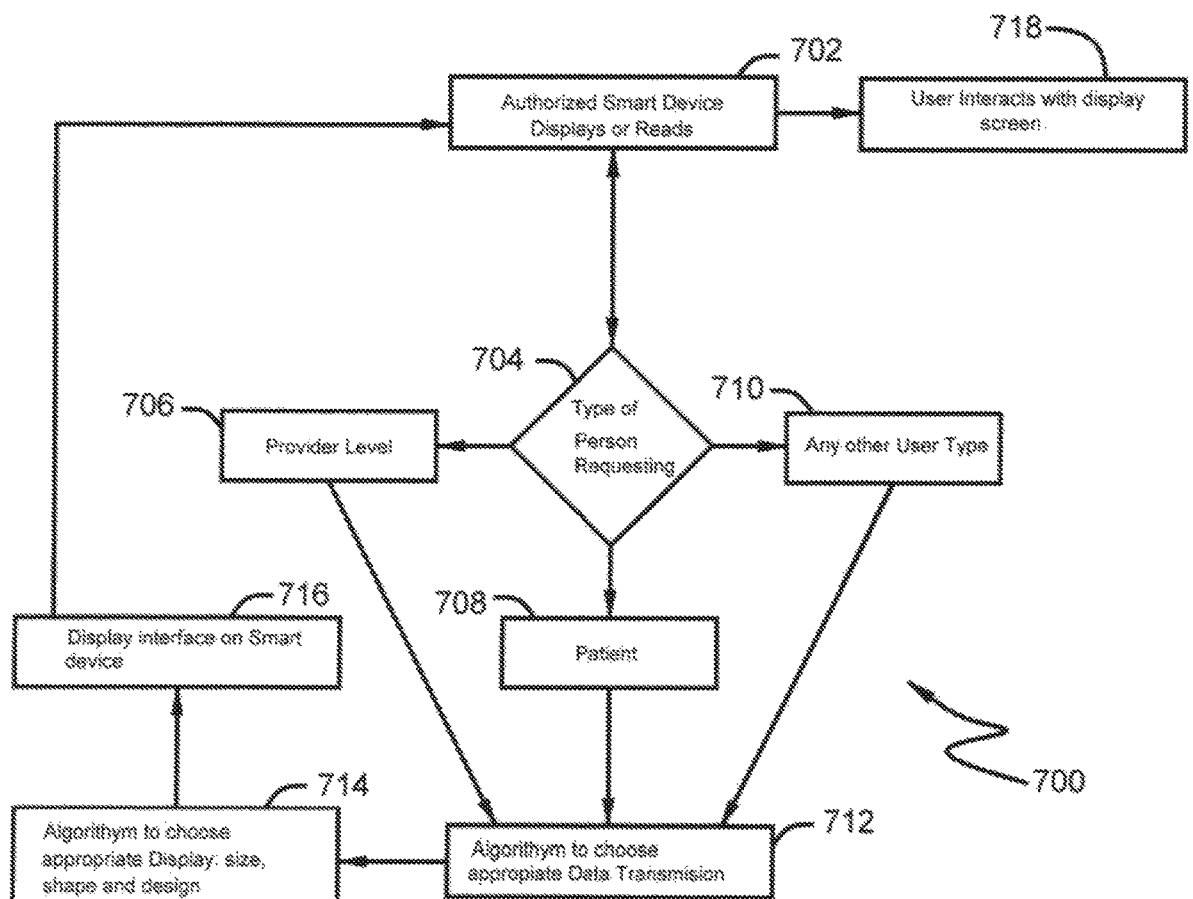
FIG. 9 shows a preferred embodiment of the security and display protocols used in the process of FIG. 4*a*.

Referring to FIG. 9, subroutine 700 shows in detail the method for verifying level of access to the central processing server 214. At step 702, CID 110 is scanned by a smart device to identify the user and device. At 704, the information is sent to the central processor 214. The identifying information of the device and user is verified. Then at step 706 within the CP, an algorithm is used to identify the individual as well as the category of person requesting the information—Patient, Healthcare Provider, Nurse, Support Staff, Family Member, Administration, Billing, Emergency Personnel or any number of other possible departments that would have reason to scan CID 110—with the individual associated with their unique login code. A doctor at step 706 in accordance with the preferred embodiment of the invention establishes medically related aspects of the treatment regimen.

At step 712 an algorithm determines what information will then be relayed back to the smart device and made visually available. The algorithm will factor in countless other variables and predetermined rules to determine the most likely information needed to be displayed. At step 714, the appropriate display is chosen. At step 716 the algorithm will also be able to count the number of interactions with the system by adjusting the information displayed based on the quantity of scans. For example, for the first scan there is a welcome screen displayed, for the second scan a welcome back screen is displayed. At step 718, the user interacts with the display screen. If the same request is put in several times the algorithm can predict an issue and runs through steps 704-716 again to better give the information requested. The user can also ask of assistance is needed and offer a help button. Once the user logs off, the interaction is complete.

Figure 10:
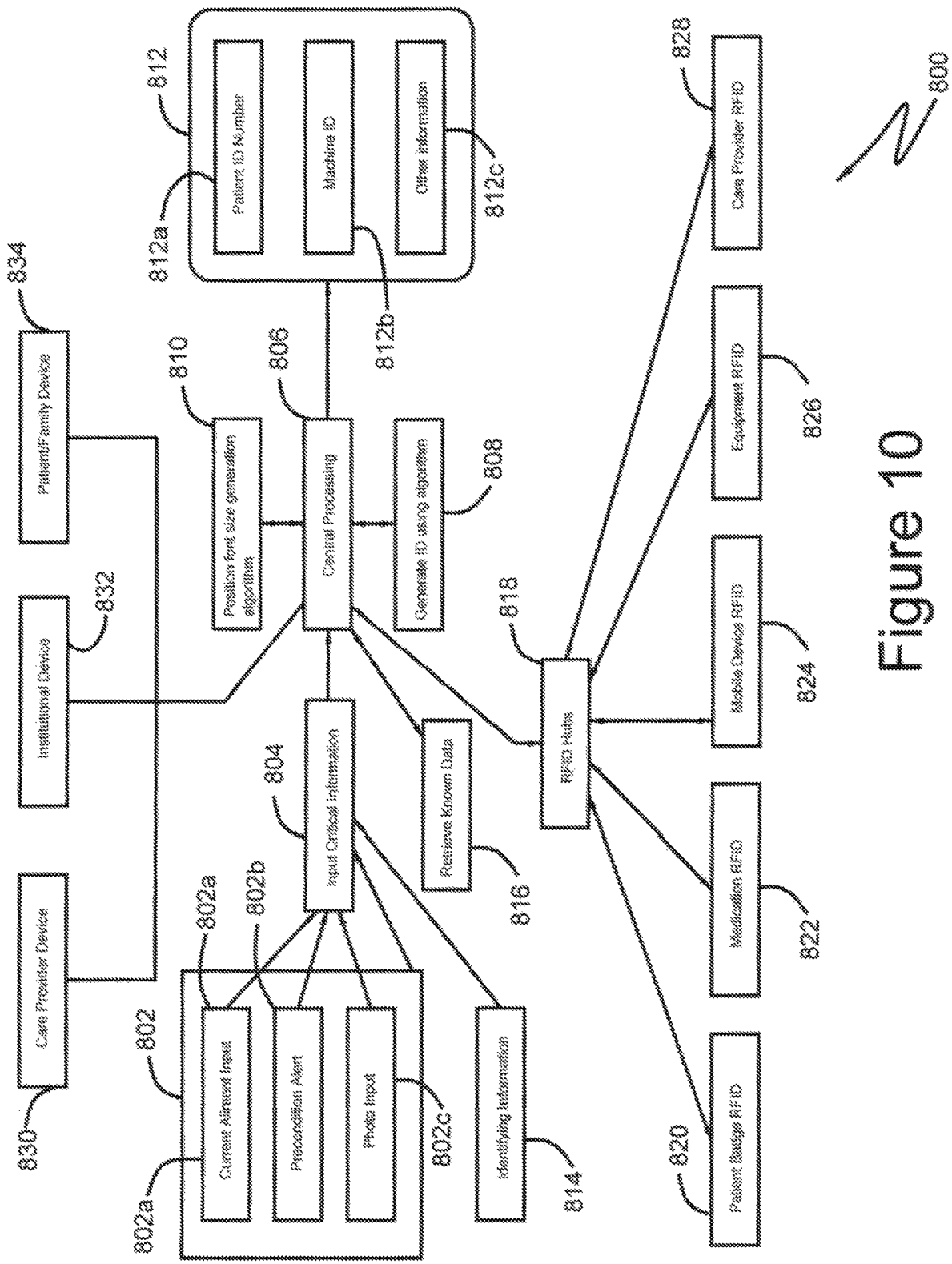
FIG. 10 is a more preferred embodiment of an intake method utilized process of dealing with a plurality of devices utilizing noncontact communication devices such as RFID.

FIG. 10 shows in greater detail an alternative embodiment of the details of new record creation step 314, wherein CID 110 further comprises an RFID chip. At step 802, the critical information is gathered that is needed to generate CID 110. Such information may include current ailment input 802*a*, pre-condition alert (including allergies) 802*b*, photo 802*c*. At step 804, the critical information is input. Then at step 806 the information is sent to the central processor 214 for storage and processing. Then at step 808, a new patient ID number is generated using a machine ID generation algorithm. Then at step 810 an algorithm is used to determine position, font, size to decide the positioning of the printing.

The identification number assigned at step 808 together with information gathered at step 804 is then sent to a central storage point 214, for example, or a plurality of storage points, dependent upon the infrastructure of the facility where the inventive method is being implemented. Ideally, such information is stored in a central server for regular update and for providing such information in response to information retrieval requests, as appears more fully herein below. The information collected at step 804 may, optionally, include such information as patient allergies, current medications, chronic conditions, and medical history. Likewise, family history with respect to conditions likely to present risks to the patient, such as diabetes, heart disease, Parkinson's disease, and so forth, are also gathered at step 814, 802*a*, 802*b* and 802*c*. In addition, the patient's reason for coming in for medical treatment is also gathered at step 802*a* for entry into, for example, the single database.

After basic information has been gathered from the patient and stored in the appropriate database, either immediately or at a subsequent appropriate point, the patient badge design sent to printer 216. In accordance with the invention, at step 812, central server 214 also generates an identification number and machine-readable identification, such as a barcode, using a generation algorithm. In an alternative embodiment, the identifying number could be the unique code pre-populated on an RFID chip or like device. As described above, this information and other information input into the system is used by central server 214 to generate a patient badge design which is stored, along with other information in central server 214.

More particularly, information respecting location of patients is gathered from patient badges 110. Location information for bottles or packages of medication bearing RFID tags 822 is also gathered by the system. Similar information for the location of caretaker mobile devices is collected at transponder 828, which is attached to the respective mobile device. Equipment whose location may change receives an RFID transponder 818. Similarly, care providers may advantageously be provided with badges, such as clip on badges of a permanent nature bearing RFID transponders 826. This may indicate the absence of needed personnel in a given area or be used to determine which healthcare provider may be messaged or alarmed to proceed to a given area to address a need or critical need, for example one generated from the system in response to the system's monitoring instrumentation connected to a patient or historical data respecting a patient, advantageously, for example, monitoring of such information using an artificial intelligence algorithm.

The integrated system and associated method provides the opportunity for remote monitoring to reduce the need for visits to the doctor or visiting nurse services. Most advantageously, the system can also reduce a patient's time in the hospital, where there are real risks of secondary infections. Deaths linked to hospital infections represent the fourth leading cause of mortality among Americans, behind heart disease, cancer and strokes. These infections kill more people each year than car accidents, fires and drowning combined. Integrated system 200 comprising secure CID 110 will likely reduce a patient's need to be in the hospital by allowing for a smooth transition of care to a facility. When the patient is discharged to their home, better home management will lead to fewer readmissions, which are not only costly and inefficient but also risky. The integrated system with CID 110 as the nexus of the system allows a secure line of communication with the hospital and the patients even during the transition and after discharge facilitating earlier discharge and less readmissions.

In accordance with the invention information from transponders 820-828 is sent by way of RFID hubs 818. Hubs 818 may be placed at various locations, for example, in the patient's room, and a nursing station, and so forth. The range of RFID hubs 818 may be varied. For example, an RFID hub attached to the bed of the patient may have a range limited to the immediate vicinity of the bed. In this manner, it may determine which bottles of medication pairing RFID transponders 822 have entered the vicinity of the patient's bed. This information is relayed to central processing unit 214 at step 806 for storage in storage device 214. Periodically, all location information is processed by algorithm 808, which uses the location information to detect potential problems. In accordance with the invention it is also contemplated that RFID information may be used for other purposes. For example, the personal computer of the family of a patient, or a smart phone 834 owned by a family member may be signaled when, for example, a patient's location has changed from the operating theater to the patient's room, by emailing a message to smart phone 834 saying that the family member has been moved from the operating room to a private room and, optionally, giving or confirming the location of that room. The message may further indicate that visitation may be had at certain hours. Thus, the ability may be provided to provide a badge, which carries an RFID chip (or some other technology). This may be used to set off an alarm if a child is removed from a designated area. Also, the same may advantageously be used as a potential "tracker" so that hospital staff know where a patient is on a floor or in a building. In other embodiments, an alternate noncontact communication system will be used to perform the same function as the RFID devices and hub.

The interaction between any individual scanning CID 110 and CID 110 can be adjusted and tweaked to fit the individual needs of the individual requesting the information. Once the information is displayed the interface will allow for other information to displayed through a navigation screen. Although completely customizable, in preferred embodiments, the navigation screen for a patient can display medication, appointments, emergency request, help button, discharge notes and instruction, scans, next appointment, frequently asked questions etc.

Providers, administration and other healthcare staff can also use CID 110 to gather information regarding the patient, next steps, appointments, primary doctors, discharge dates, previous notes, instructions, treatment plan etc.

Meanwhile the central server 214 manages and organizes this data so the appropriate information can be pulled when necessary. Once scanned with a properly configured smart phone the central server 214 will pull the appropriate information given the individual who scanned and the goal of the interaction. This critical information will be displayed on the device. RFID and QR codes are currently used in healthcare but are often disjointed and designed for single systems. As a result, a bar code may only be compatible with one system and a second code may be needed for additional systems. This creates confusion and opportunities for error. Since each CID is unique and can be encoded with a unique identifier, healthcare systems can use the same identifier inside and outside of the healthcare facility. By integrating the disparate systems to connect to the CID platform the facility can use a single code for each patient regardless of the location. In one embodiment, the code is a unique URL. Therefore, when the patients are transferred the same code used by the hospital can be used by the patient smart device or any other reader. The smart device with launch a web browser and the unique URL will allow for access to information. The confidentially of the data shared will depend on the protocols taken to secure the device is associated with the patient. In a controlled setting or through an app the CID platform can easily manage the request using the same URL code the patient would use outside of the application. This gives an incredible amount of flexibility and functionality to the patients, facilities and other systems that interact with the device and this robust functionality is only capable with a unique identifier at the nexus of care.

The information can vary based on who is scanning the device. For example, a patient can scan their own CID and be given pertinent information about their care.

Currently, common practice in a discharge scenario, the individual being discharged from the healthcare facility will be given verbal instructions on what the next steps are and a stack of medical documents. With this invention, CID 110 will remain on the individual. When tapped with a smartphone all instructions and pertinent information will be readily available. This information will be pulled from the central server 214 and uses CID 110 as a verification point.

Since the CID is nontransferable and will be destroyed if removed or otherwise tampered with, the system can immediately and securely verify the individual's identity even remotely just by simply having a successful scan from an authorized device. Thus, caregivers, pharmacies and other service providers can use the functional CID 110 as a way to securely and reliably confirm the identity to provide remote care including administering remote medication. Although remote monitoring already exists in many forms, no one has found a way to securely identify the individual remotely to enable these devices securely and seamlessly. Thus, a patient who is at home can be managed remotely as all that is needed is for someone to scan CID 110 with a smart device to confirm the identity of the patient. This is particularly advantageous for patients who are immune compromised, heart patients, diabetics, in post op recovery, as well as patients who have communication challenges, or otherwise need robust staffing as the secure identification device combined with the remote monitoring eliminating human communication error, so a layperson can manage care more easily. In a preferred embodiment, CID 110 is Bluetooth enabled (with and without a battery) and is automatically paired to confirm connection is within range of the care/monitoring device(s) thus scanning is not necessary and if the connection is somehow severed, an alarm is sent to a nearby facility to then send staff to checking functionality. This is discussed further below.

In the case of a patient going home, the patient will have direct access to the discharging facility including interactive information reservoir which can notify the patient of but not limited to medication schedule, appointment reminders, wound check, emergency 911, schedule an appointment, frequently asked questions, or even be able to ask a question to a healthcare provider. In the case of interdepartmental or facility transfers, the individual will use CID 110 to navigate through the transitional process while the transition destination will use CID 110 to confirm the arrival of the correct person in the correct setting. This allows healthcare providers to quickly and accurately not only identify patients but also know where they should be at any time creating an infrastructure that puts the individual as the nexus point for care.

This system is unique since it securely verifies the patient in a controlled setting, such as a healthcare facility than uses that identification device, CID, to manage the individuals transition from any origination point to any transitional destination.

This centralized and secure system allows for 1) regular data acquisition (continuous or discrete) anytime, anywhere; 2) fast transmission of the acquired information to all team members for processing and comparison with previously acquired serial data (including individual baseline data); 3) fast and accurate processing, analysis, and accurate detection of serial changes; and 4) transmission of the results back to personal devices (held by the individuals and medical personnel) to inform them and perhaps adjust the monitoring thresholds.

The system of the present invention can be used for management and analysis of electronic health (medical) records and information, analysis and management of biometric data, or information management of other types of healthcare data. The system of the present invention provides instant access to information from a variety of distributed sources to reduce costs, improve quality of patient care and optimize decision-making ultimately resulting in safe, better, efficient care of the patient. For example, the system can be used to provide a real-time view of in hospital patient distribution and operations structure in different departments and at different stages of the treatment process, from admission to transfer to discharge, or in the emergency room. In preferred embodiments, the system can capture and integrate monitoring of vital signs, biometrical data, capture and integrate text, images, technical information related to device functioning and instrumentation status. The system can also provide an intelligent, tailored representation for different types of users and different points of care. For example, it can improve information sharing among the healthcare providers, including physicians, nurses, technicians, clerks, and others. The system of the present invention can also facilitate analysis, management, and optimization of information processing.

The system also may also be used in connection to providing patient access to medication via connection to a pharmacy with a delivery service. The system already includes collecting patient medical information from a patient computer, securing the patient medical information and sending the secured patient medical information from the patient computer to a remote computer. The addition of real time information from nurses and caregivers can be part of a remote examining the patient and with proper review of the patient medical information, the system may generate a prescription for the patient and send the prescription to a pharmacy.

Likewise, the above system may be merged with physiologic sensing technologies to create a patient ID that not only conveys identification and medical information, but also engages in real time, wirelessly transmitted, physiologic sensing and databasing of information, i.e., morning blood draws to find out the patient's blood chemistry status, etc. for example, a colorimetric oxygen sensor may be incorporated into the inventive badge, and applied to the chest of the patient. Other physiologic states can be measures as well such as temperature, glucose and gyroscope measuring angular movements and velocity as an example.

In preferred embodiments, applying intelligent analysis and optimizing diagnosis and treatment, including diagnostic and treatment plans and providing intelligent alarms and alerts to support and optimize clinical decision-making. The biometric (physiological and health) data may gathered by professionals who are collecting and inputting information into the system or in alternative embodiment can collect real time from a variety of sensors including vital sign monitors, ventilators, infusion pumps. The smart devices may include devices for acquisition and analysis of electrocardiogram, electroencephalogram, electromyogram, blood pressure, impedance, vascular resistance, cardiac output, biochemical, genetic, proteomic, molecular, and other types of health and environmental data. The system would be designed to accept and recognize new data from wireless physiological sensors in addition to the integrated barcode scanning or RFID tag or other tags or other types of automatic entry of information at the bedside in a real time. The system of the present invention can also adapt, compare and merge new information with the existing data in the system. This information can also be transmitted individually using NFC RFID and UHF RFID or the technologies can be combined into a single chip. NFC is passive technology which requires an action by the user or a device to power the NFC chip to deliver the signal. UHF is also passive with longer read distance. Additionally, Bluetooth functionality can be used which historically can be active meaning in combination with a battery the device can send out its own signal. This is an issue in healthcare since batteries are not MRI compatible of biocompatible. By eliminating the battery and using ambient radio waves in the atmosphere, Bluetooth can be added to the CID to create an active battery-less solution. This solution would allow for secure communication with smart home devices for seamless identification which will greatly enhance the efficacy of home health care and other health services administered outside of a hospital or other controlled environment.

This system may be particularly advantageous for vulnerable (e.g. fall risk) patients who leave the hospital and have specific information on their device pertaining to their self-care at home. In preferred embodiments, the system can link up with other companies to offer services (e.g. home healthcare, housekeeping, PCA, etc.) necessary to prepare the home for these particular risks associated with patient.

In the practice of this invention, health related information is preferably monitored on a periodic, or quasi-periodic basis, meaning that data is taken or read and recorded periodically. The periodic recording of data may extend for short periods such as hours or days (depending on the data needed), or may extend over a longer period. Herein "health related information" is used generically to mean all forms of information relating to health, including physiological data that include but are not limited to blood pressure, cardiac output, vascular activity, temperature, respiration, cardiac, abdominal, and other electrical, mechanic, sonic, biochemical, and biophysical processes in the human body, as well as other information related to human life, including demographic (age, gender), environmental (pollution, job conditions), and psychological data, life styles, exercise activities, etc. Tracking changes in health or medical data, using individual's own data as a personalized reference, allows one to improve the accuracy of medical diagnosis.

Comparing current data with individual's historical test results, such as previous electrocardiogram (ECG), blood pressure, heart rate, etc., helps physicians in differentiating acute changes, which usually require proactive management, from chronic abnormalities. In addition, comparison with individual's historical data also helps in exposing subtle or gradual changes. For example, patients with chronic ischemic heart disease often have gradual narrowing of coronary arteries, which is associated with gradual, subtle changes in the electro cardiographic STT-complex, which are difficult to detect. Other symptoms may include slowly diminishing tolerance to physical exercise, which can also be difficult to detect.

The system allows certain designated people such as a family member, a friend, or a neighbor to informally check on the well being of the patient. The system is also effective in containing the spiraling cost of healthcare and outpatient care as a treatment modality by providing remote diagnostic capability so that a remote healthcare provider (such as a doctor, nurse, therapist or caregiver) can visually communicate with the patient in performing remote diagnosis. The system allows skilled doctors, nurses, physical therapists, and other scarce resources to assist patients in a highly efficient manner since they can do the majority of their functions remotely. Additionally, a sudden change of activity (or inactivity) can indicate a problem. The remote healthcare provider may receive alerts over the Internet or urgent notifications over the phone in case of such sudden accident indicating changes. Reports of health/activity indicators and the overall well-being of the individual can be compiled for the remote healthcare provider. Feedback reports can be sent to monitored subjects, their designated informal caregiver and their remote healthcare provider(s). Feedback to the individual can encourage the individual to remain active. The content of the report may be tailored to the target recipient's needs, and can present the information in a format understandable by an elder person unfamiliar with computers, via an appealing patient interface. The remote healthcare provider will have access to the health and well-being status of their patients without being intrusive, having to call or visit to get such information interrogatively. Additionally, remote healthcare provider can receive a report on the health of the monitored subjects that will help them evaluate these individuals better during the short routine check up visits. In preferred embodiments, the system can perform patient behavior analysis such as eating, drinking, activity and medication compliance, among others and alert appropriate healthcare providers on the patient's team.

CID 110 is also effective as a data collection and immediate feedback tool. All patients wearing the CID will be able to interact with CID 110 and receive a unique identity specific interface. This interface can display any number of experiences including surveys. In this embodiment, CID 110 is used as a feedback and data collection tool to get feedback from patients in real-time and specific by location. Healthcare systems can tailor this data collection to answer enterprise wide concerns or zone in on issues that are relevant to a particular facility or department. Furthermore, the feedback can be tailored to change based on the patient and countless other variables and possibilities.

The system also may also be used in connection to providing patient access to medication via connection to a pharmacy with a delivery service. The system already includes collecting patient medical information from a patient computer, securing the patient medical information and sending the secured patient medical information from the patient computer to a remote computer. The addition of real time information from nurses and caregivers can be part of a remote examining the patient and with proper review of the patient medical information, the system may generate a prescription for the patient and send the prescription to a pharmacy.

Other Applications

While a preferred embodiment of the inventive method and system can be useful in the transfer of patients who are transferred from one location to another, the inventive method and system can be extended to for broad application on other settings including hotels, amusement parks, travel, recreation, even short-term situations such as sporting events and concerts.

The inventive method and system with its unique identification system bonded to the surface of the skin securely identifies an individual in any setting where temporary identification is necessary or beneficial and incorporates cloud data management software to efficiently and effectively manage the flow and location of the individual as they transfer from one destination to another. In addition to the uses noted above, the invention is particularly useful when used in connection with people with disabilities who are in residential settings/group homes for disabled adults and children. Many of these individuals are not verbal and are often not staffed consistently at their schools, residences, homes and of course when they need medical care, their medical facilities. Furthermore, many of these same individuals often need to travel outside of their local area to get the specialized medical care needed to keep them healthy. Regular communication between all of the team members, a group that can include daytime teachers, evening teachers, in house and outside therapists, residential staff, parents, in house and outside doctors, out of town specialists is often cumbersome, inaccurate, delayed and in general quite unmanageable. For many children or adults with developmental disabilities, the management of medical care, psychiatric, educational therapies and behavioral therapies is further challenged when they are in a residential facility. The use of the inventive system is particularly helpful to ensure that all of the various providers input information put into the system in real time or close to as possible so that at any point, accurate information is available for parties to view and access to some or all of the information is given depending on the identity of the inquirer.

Take an example of a child or adult in a residential school that has a seizure disorder, an autism diagnosis, and is non-verbal. In the course of one day that student may work with eight or nine people for various services at two or three different locations. That same student may come back to his or her own home for a visit. A parent just may want a view into a child's day or week while they are away from home or before they come home for a visit. Currently such information is often passed haphazardly, by telephone. Sometimes these home visits are to see a medical specialist. Thus, when a parent takes a child to see their psychiatrist or neurologist, there may be a request for specific information regarding a patient's behaviors (specific nature, timing, intensity, duration) to consider adding or adjusting a patient's medication. A parent or guardian, despite everyone's best efforts, may not be able to provide the information needed to make such critical decisions. The integrated system gives a parent or caregiver a chance to see what is happening with the child on regular basis and share the information with parties as needed. Additionally, when the child goes on vacation with their family, CID 110 can be printed with additional information so that when a family goes to an amusement park, if the non-verbal child gets lost, any park or place with an internet connection can see a CID saying the person is non-verbal and then can scan the QR code and get basic information needed for next steps (e.g. contacting the caregiver, a hospital, the police, a facility). Temporary CID 110 is a far less invasive security measure than physical systems such as personal locator bracelets, which are fitted to one's wrist or ankle. Parents are often unable to use these because their child is unable to tolerate the device and also because the system only works when local law enforcement is tied into the system. While the inventive system can be customized at many levels and uses multiple algorithms to selectively give access to information, the use itself is very simple as Internet access is almost ubiquitous. Even in international locations, Internet access is readily available and the QR code for example is almost universally known. Further the temporary nature of CID 110, allows the identification to be customized to have information in different languages if someone is traveling.

Furthermore, it would be safe to use as a long-term solution for identification as opposed to implants and other invasive solutions. As stated above CID comprises ink and adhesive and would be printed on a printable substrate. Preferably, CID 110 has contrasting background, such as white, cream or yellow not only to draw a contrast between words and lettering but for the easy identification of quadratic codes, barcodes and data matrix codes. Furthermore, with a white background, CID 110 is better suited for reading detailed information on any skin type of color contrast, and tends to be more durable because the marking to background contrast is better preserved with a white background and are more visible and versatile when it comes to what can be put onto the CID such as words, numbers, images or specific color combinations. As it is anticipated that for long term use such as the long-term care situations described above, a skin safe ink or toner would be used in connection with printer 216. The invention contemplates the use of a plurality of colorants with the potential of excellent full-color reproduction, suitable non-reactive colorants include, for example metal oxides, such as black iron oxide, yellow iron oxide, red iron oxide, titanium dioxide, zinc oxide, ultramarine as well as zinc oxide and the like which may be used to approximate a good image color. The adhesive used in CID 110, may be printed on the printing sheet would also be a skin safe adhesive such as a biocompatible acrylic, silicone or cyanoacrylate.

Printer 216 may print the adhesive and part of the RFID or the carrier sheet may already have those elements. Pre-manufactured carrier sheets with adhesive substrate and contrasting background may also be used with the variable data added at point of service. Additionally, the substrate would be waterproof.

The inventive system and method is very flexible depending on the needs of a patient and/or the facility. If there is a patient with robust medical needs, it would be reasonable that relevant information would be kept locally and that different information would be stored locally depending on the needs of the patient. In other words, just as CID 110 can be personalized, so too the database updates, the user interface and options can also be personalized. Requests for information can be sent to any "member" of the system for any information at any time and depending on the clearance of the requester, that information can be sent either directly (where all we need is clearance from the central server) or via the central server. The secure, non-transferable, securely affixed to the patient's skin identification is verified before being activated and allows for a transfer of information that would otherwise be feasible as those sorts of risks cannot be taken with a such a centralized system. In other words, the patient is always at the center of care and any transfer or disclosure of information and thus would be providing consent. While CID 110 is incredibly secure, it is also non-invasive and temporary. A comparable level of security with an identification device would perhaps be an implanted chip, which is conceivably transferable, highly invasive and risky making implants for security highly impractical. In connection with the inclusion of RFID (or other noncontact communication device), CID 110 security and functionality is further enhanced.

CID 110 would durably adhere to the skin to provide useful information such as visually readable data, data codes such as Quick Response (QR), data matrix or bar codes. Such information can be read with an optical electronic device, electronic devices using non-contact communication technology and data processors such as circuits, microchips and microprocessors and security components for authentication. Visually readable data, which can be read with the human eye, generated using dye, ink or toner can be applied using any number of printing techniques including sublimation, thermal, laser or inkjet printing.

Electronic devices using non-contact communication technology such as but not limited to RFID and Bluetooth. These microchips can store significant amounts of information. These identifiers can be random generated codes which when used with a data management system will allow identification, tracking or data manipulation. These codes can serve as a secure form of data communication allowing the reader to pull information from the skin worn device and also communicate back with the device.

These devices add a level of security and functionality over optically read codes. These devices can store more information, be reprogrammed, keeping a rolling count of the number of times the device was read. This functionality creates any number of advantages given the application. The rolling code in addition to counting can also dynamically change the information being displayed based on the count. Furthermore nano-sized RFID particles can be added at this stage used to confirm the authenticity of the skin worn device.

Data processors such as circuits, microchips and microprocessors can be added to the device in conjunction with a conductive ink to create a skin wearable computer-processing unit. Security components such as holograms can be added in the final step for authentication ideally in layer. In one embodiment, the near field communication RFID or Bluetooth device are incorporated in the carrier layer prior to printing the cutaneous device.

With a strong foundation of secure patient identification other third-party systems and sensors can be integrated in to the CID to further access medical diagnostics at any location while certifying the identification of the individual being treated. This cannot be done with a wristband, because a wristband is often removed directly after the hospital stay as regular practice. Furthermore, the wristband is unconformable and intrusive. The wristband can be easily replicated and the once removed the wristband is still in tact and it would be a security risk to build a care foundation on such an unreliable and antiquated form of identification. In the case of wristbands with RFID, has more functionality, however the inherent challenges with the wristband still exist. Adding RFID technology to a wristband does not manage the patient it manages the wristband. The inventive CID is located directly on the surface of the skin. The CID cannot be transferred. The CID if placed on the patient properly offers unparalleled security when identifying an individual. Each facility or location uses this device to properly transition the patient from one facility to the next location wherever it may be. Furthermore, there is a need for caregivers and sometimes the patients themselves to be able to access a system where important information can be sent to and received from medical providers. The CID offers a mechanism to allow this transfer of protected health information in a secure way ensuring that the data is being send to the appropriate individual. The inventive system's unique characteristics including its secure identification device combining a centralized connected database with a make it the only viable option to make patient the focal point of the system building system of care around the ability to securely identify the patient in any location at any time during the care cycle.

The processing functions of the system in the foregoing embodiment can be realized in hardware or software. Not only are all of these processing functions realized by the hardware or software, but also part thereof may be realized by using the hardware or software. That is, any combination of the hardware and software may be adopted.

With respect to the foregoing embodiments, various modified examples are conceivable within the scope of the gist of the invention. Besides, various modified examples and applied examples created or combined based on the recitation of the specification are also conceivable. It should be understood by those skilled in the art that various modifications, combinations, sub-combinations and alterations may occur depending on design requirements and other factors. It should be understood that various changes and modifications to the presently preferred embodiments described herein will be apparent to those skilled in the art. Such changes and modifications can be made without departing from the spirit and scope of the present subject matter and without diminishing its intended advantages.

What is claimed is:

1. A system for identifying and providing for the retrieval of information relating to an individual by a plurality of authorized users at multiple facilities, comprising:
   a) a skin wearable, waterproof, non-transferable frangible individual identification device comprising an adhesive and an ink arranged to provide a physiologically perceptible, humanly understandable, and machine-readable information relating to said individual wherein once applied to skin said identification device is not removable in one piece;
   b) a plurality of reader devices;
   c) a computer interface device receiving information from said individual identification device and from said reader devices respecting the individual identified by said individual identification device;
   d) a computer system coupled to said computer interface device, said computer system including a memory with an algorithm for processing information collected by said computer system; and
   e) comprising a separate set of reader devices and a separate service rendering system, each output information from their respective reader devices to a common database, the contents of said common database being coupled to a computing device which communicates information to said plurality of facilities.

2. System as in claim 1, wherein the system is part of a medical facility and further comprising:
   (f) a database containing treatment information;
   (g) a communications link outputting information to a mobile device respecting medical treatment;
   (h) a communications link outputting information to a mobile device respecting personal or sensitive information;
   (i) said communications link being coupled to receive from said mobile device an indication that said healthcare service has been performed; and
   (j) clock means for confirming performance of said healthcare service after a period of time.

3. System as in claim 1, wherein when admitted to a first facility the individual identification device is affixed to the individual and associated demographic information, medical information is gathered and input into the computer system, associated with the individual identification device and stored in the system for future access.

4. System as in claim 1, wherein when an individual is transferred from the first facility to a second facility, the individual identification device is on the patient and the computer system is accessible by the second facility.

5. System as in claim 2, wherein when a patient is transferred from the one facility to another facility, the individual identification device is on the individual and the computer system is accessible by the second facility.

6. System as in claim 1 wherein said identification device is effectively tactically imperceptible and comprises an adhesive layer and an ink layer containing individual specific information which can be visually seen or read including an embedded two-dimensional code, wherein said code can be scanned for patient identification, interaction, information exchange, and instructions.

7. System as in claim 1 further comprising a non-contact communication device.

8. System as in claim 2, wherein the patient is transferred from a healthcare facility to a non-healthcare residence, the identification device is scanned to identify the patient and administering care.

9. System as in claim 1, when used in conjunction with an authenticated smart device can serve as a two-point identification system allowing access to secure information or to bypass a log in or sign up process.

10. System as in claim 2, wherein said computer system algorithm includes means for one or more of the following functions: electronic medical records management, authentication and authorization to access said medical records, imaging modality management and picture archiving and communication system, patient care management including monitoring, messaging, scheduling, resource allocation, knowledge integration, back-up and disaster recovery services, inventory and order management service for both materials and drugs, side effects of drugs, interactions among drugs, and interactions among drugs and food, telemedicine for remote medical diagnosis and treatment with integrated video conferencing, automated mechanisms for admission, discharge, and transfer of patients.

11. System as in claim 1, wherein said computer system algorithm includes means for authentication and authorization using an alphanumeric code, smartcards or biometric means.

12. System as in claim 1, wherein said computer system algorithm includes means for displaying information using a display, wherein displaying comprises visually emphasizing and sorting the electronic case information based on an authorization level of user.

13. System as in claim 2, wherein said computer system algorithm includes means for connecting medical equipment to a portable wireless transmitter for transferring status data from said medical equipment to said transmitter, wherein said transmitter in turn transmits said status data to said wireless receiver.

14. System as in claim 1, wherein each communication or request from a particular mobile device includes a secure device code identifying that mobile device to the system.

15. System as in claim 1, wherein said computer system algorithm includes means for sending reminder messages for medications, appointments, and other tasks.

16. System as in claim 15, wherein said computer system algorithm includes means for asking for confirmation that medication was taken.

17. A method using the system as in claim 1, when admitted to a first facility the individual identification device is affixed to the person and associated demographic information and other relevant information is gathered and input into the computer system, associated with the individual identification device and stored in the system for future access.

18. A method using the system as in claim 1, wherein the individual identification device is affixed to person and associated demographic information and other relevant information is gathered and input into the computer system, associated with the individual identification device and stored in the system for future access.

19. A method using the system as in claim 1, when a patient is transferred from the first facility to a second facility, the individual identification device is on the patient and the computer system is accessed by the second facility.

20. A method using the system as in claim 1, when a patient is transferred from the first facility to a second facility, the individual identification device is on the patient and the computer system is accessible through the Internet.

21. A method to manage the transfer of information related to a patient wearing a cutaneous identification by assisting authorized users in accordance with a remote request for processing previously acquired and patient information and data and to store and retrieve patient specific information in real time using a cloud based central server comprising an information storage and processing system with a plurality of databases, said method comprising the steps of:
(a) providing a cloud based central server comprising an information storage and processing system including a secure database
(b) sending a communication to the central server when an authorized user using an authorized device capable communicating through a cloud-based network scans the identification device;
(c) confirming that the patient has a medical record stored in the central server by retrieving comparing patient information to information in the secure database;
(d) identifying the user and confirming authorization of the user to access central server by retrieving comparing user information to information in the secure database;
(e) identifying the device and confirming authorization of the device to access central server by retrieving comparing device information to information in the secure database;
(f) confirming that the user has the clearance to retrieve information patient has a medical record stored in the central server by retrieving comparing user and patient information to information in the secure database;
(g) receiving from the authorized device a request to retrieve information from or add information to said secure database;
(h) communicating the request to the central server;
(i) translating the request to locate the information from the secure database;
(j) confirming level of authorization of the user to determine the subset of the medical record accessible to the user to determine retrievable information by retrieving comparing authorization information to information in the secure database;
(k) retrieving the retrievable information from the secure database;
(l) transmitting the retrievable information via the central server the retrievable information to the authorized device; and
(m) updating the medical record in central server with any changes and wherein the cutaneous identification device is a skin wearable, waterproof, non-transferable frangible individual identification device comprising an adhesive and an ink arranged to provide a physiologically perceptible, humanly understandable, and machine-readable information relating to said individual wherein once applied to skin said identification device is not removable in one piece.

22. Method according to claim 21, method further comprising transmitting a notification to medical personnel that the patient medical record has been updated.

23. Method according to claim 21, method further comprising transmitting a notification to some authorized users that the patient medical record has been updated.

24. Method according to claim 21, wherein the secure database is comprised of multiple databases.

25. Method according to claim 21 wherein when receiving repeated request for data, processors adjusts displayed data parameters.

26. Method according to claim 21, further comprising, monitoring physiological parameters of a patient by coupling a patient monitor having a memory component and a connected device having a means to connect to the central server to said patient, to monitor at least one said physiological parameter periodically transmitting the physiological parameters from said patient monitor to the central server; storing physiological data in the central database and selectively transmitting physiological data to authorized devices.

27. A method according to claim 21, wherein a third party connected device from an entity independent from and not controlled by the user, can send information to the central server.

28. A system for identifying and providing for the retrieval of information relating to an individual by a plurality of authorized users at multiple facilities, comprising:
  a) a skin wearable, waterproof, non-transferable individual identification device comprising an adhesive and an ink arranged to provide a physiologically perceptible, humanly understandable, and machine-readable information relating to said individual wherein once applied to skin said identification device can be remotely deactivated to render said identification device inoperable;
  b) a plurality of reader devices;
  c) a computer interface device receiving information from said individual identification device and from said reader devices respecting the individual identified by said individual identification device;
  d) a computer system coupled to said computer interface device, said computer system including a memory with an algorithm for processing information collected by said computer system; and
  e) comprising a separate set of reader devices and a separate service rendering system, each output information from their respective reader devices to a common database, the contents of said common database being coupled to a computing device which communicates information to said plurality of facilities.

29. System as in claim 28, wherein the system is part of a medical facility and further comprising:
  (f) a database containing treatment information;
  (g) a communications link outputting information to a mobile device respecting medical treatment;
  (h) a communications link outputting information to a mobile device respecting personal or sensitive information;
  (i) said communications link being coupled to receive from said mobile device an indication that said healthcare service has been performed; and
  (j) clock means for confirming performance of said healthcare service after a period of time.

* * * * *